United States Patent
Sweis et al.

(10) Patent No.: US 11,596,672 B2
(45) Date of Patent: *Mar. 7, 2023

(54) HYALURONIDASE COMPOSITIONS AND METHODS OF USING SAME FOR ASSESSING AND/OR TREATING PERIORBITAL PUFFINESS

(71) Applicant: Standard of Care Corporation, Chicago, IL (US)

(72) Inventors: Iliana E. Sweis, Chicago, IL (US); Bryan C. Cressey, Chicago, IL (US)

(73) Assignee: STANDARD OF CARE CORPORATION, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/840,250

(22) Filed: Apr. 3, 2020

(65) Prior Publication Data

US 2021/0154274 A1    May 27, 2021

Related U.S. Application Data

(60) Provisional application No. 62/940,747, filed on Nov. 26, 2019.

(51) Int. Cl.
*A61K 38/47* (2006.01)
*A61P 29/00* (2006.01)

(52) U.S. Cl.
CPC ............. *A61K 38/47* (2013.01); *A61P 29/00* (2018.01)

(58) Field of Classification Search
None
See application file for complete search history.

(56) References Cited

PUBLICATIONS

Hilton et al., Eur. J. Med. Res. 19(30): 1-5 (2014).*
Garcia et al., Arch. Facial Plast. Surg. 8: 374-380 (2006).*
Zoumalan, Aesth. Plast. Surg. 43: 115-122 (2019).*
De Pasquale et al., Aesth. Plast. Surg. 37: 587-591 (2013).*
Amrith et al., Anatomy, in: Amrith et al., Ocular Adnexal Lesions, Springer, Singapore (2019).*
Hilton et al., Eur. J. Med. Res. 19: 30 (2014).*
Cavallini et al., Aesth.Surg. J. 33(8): 1167-1174 (2013).*
Wendling, "Hyaluronidase eases post-Mohs periorbital swelling," Dermatology News, Dec. 1, 2015.*

* cited by examiner

*Primary Examiner* — Erin M. Bowers
(74) *Attorney, Agent, or Firm* — Christopher J. Betti

(57) ABSTRACT

The present disclosure provides a method for treating a subject with periorbital puffiness by determining if the periorbital puffiness is due to edema or a structural change and administering a protein having hyaluronidase activity to the periorbital region of the subject if the periorbital puffiness is due to edema. Also provided are methods for determining if periorbital puffiness is due to edema or a structural change in a subject in need thereof by administering a composition that comprises a protein having hyaluronidase activity to the periorbital region of the subject, assessing the periorbital region at a predetermined amount of time after the administration of the composition, and then determining whether there is an improvement in the periorbital puffiness.

6 Claims, 5 Drawing Sheets

Specification includes a Sequence Listing.

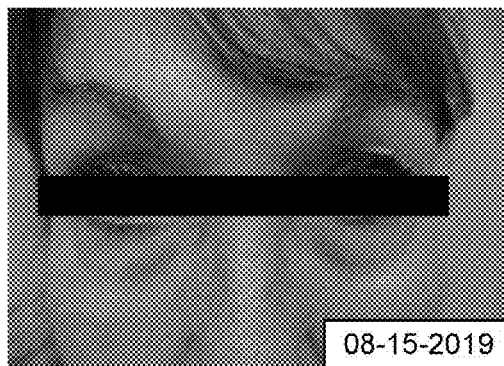
FIG. 5A  08-15-2019
FIG. 5B  09-04-2019
FIG. 5C  08-15-2019
FIG. 5D  09-04-2019
FIG. 5E  08-15-2019
FIG. 5F  09-04-2019
FIG. 5G  08-15-2019
FIG. 5H  09-04-2019

HYALURONIDASE COMPOSITIONS AND METHODS OF USING SAME FOR ASSESSING AND/OR TREATING PERIORBITAL PUFFINESS

CROSS REFERENCE TO RELATED APPLICATIONS

The present application claim priority to U.S. Provisional Patent Application Ser. No. 62/940,747, filed Nov. 26, 2019, which is incorporated herein by reference in its entirety.

FIELD

The present disclosure generally relates to methods for assessing and/or treating periorbital puffiness using a composition comprising a protein having hyaluronidase activity.

BACKGROUND

The appearance of puffiness around the eyes (e.g., bags under the eyes) is a concern to millions of people particularly as they age. It is generally believed that shifting forward (pseudoherniation) of fat pads within the orbit of the eye (two along the upper eyelid and three along the lower eyelid) is the cause of this puffiness.

Consequently, a surgical procedure (blepharoplasty) is often performed which involves the removal of segments of these fat pads from the eyelids. This surgery carries risks such as excessive fat removal leading to a hollow appearance around the eyes, over-resection of the skin leading to difficulty closing the eyes and chronically dry eyes, potential visual compromise if there is bleeding that compresses the optic nerve, and a longer recovery period. Also, if the condition of puffiness is not due to shifting of the eyelid fat pads, but rather due to swelling of the soft tissues of the eyelids or swelling of the fat pads, surgery is the incorrect procedure and will not properly address the cause of puffiness or bags. As such, there exists a need for methods to assess whether periorbital fullness is due to edema or a structural change in a subject.

SUMMARY

The present disclosure addresses the above need by providing a method for determining if periorbital puffiness (fullness) is due to edema or a structural change in a subject's periorbital region (e.g., making a determination so as to rule out one cause of periorbital edema). Advantageously, such methods may be used to determine if a subject is a candidate for treatment with a protein having hyaluronidase activity or a blepharoplasty to treat their periorbital puffiness.

Provided herein are methods of determining is periorbital puffiness in a subject is due to edema (e.g., due to periorbital edema including edema of a periorbital fat pad, a periorbital soft tissue, and/or malar region) or a structural change by administering a protein having hyaluronidase activity to the periorbital region of the subject. A determination is then made that the periorbital puffiness is due to edema and/or a structural change (e.g., a herniation of one or more of the upper and/or lower eyelid fat pads) based on whether the periorbital puffiness improves, partially improves, or does not improve as a result of administration of the protein having hyaluronidase activity.

In some embodiments of each or any of the above- or below-mentioned embodiments, the structural change is a herniation of one or more upper and/or lower eyelid fat pads.

In some embodiments of each or any of the above- or below-mentioned embodiments, no improvement in periorbital puffiness indicates that the periorbital puffiness is due to a structural change.

In some embodiments of each or any of the above- or below-mentioned embodiments, a partial improvement in periorbital puffiness indicates that the periorbital puffiness is secondary to both edema and a structural change.

In some embodiments of each or any of the above- or below-mentioned embodiments, improvement in periorbital puffiness indicates that the periorbital puffiness is secondary to edema.

In some embodiments of each or any of the above- or below-mentioned embodiments, an improvement includes a reduction in the periorbital puffiness.

In some embodiments of each or any of the above- or below-mentioned embodiments, the protein having hyaluronidase activity is hyaluronidase.

In some embodiments of each or any of the above- or below-mentioned embodiments, the hyaluronidase is a recombinant hyaluronidase.

In some embodiments of each or any of the above- or below-mentioned embodiments, the hyaluronidase is a bovine or a human hyaluronidase.

In some embodiments of each or any of the above- or below-mentioned embodiments, the step of administering is performed by one or more injections to the region of the subject having edema.

In some embodiments of each or any of the above- or below-mentioned embodiments, the step of administering comprises applying a patch or a cream to a region of the subject having edema.

In some embodiments of each or any of the above- or below-mentioned embodiments, the protein having hyaluronidase activity is administered in a therapeutically effective amount.

In some embodiments of each or any of the above- or below-mentioned embodiments, each injection includes about 1 to about 1,000 Units of the protein having hyaluronidase activity.

In some embodiments of each or any of the above- or below-mentioned embodiments, each injection includes about 5 to about 15 Units of the protein having hyaluronidase activity.

In some embodiments of each or any of the above- or below-mentioned embodiments, each injection is performed using a 0.5 mL syringe.

In some embodiments of each or any of the above- or below-mentioned embodiments, the 0.5 mL syringe comprises a 32-gauge needle.

The present disclosure also provides a method for treating a subject with periorbital puffiness, the method comprising determining if periorbital puffiness is due to edema or a structural change in a subject by administering a composition that comprises a protein having hyaluronidase activity to one or more upper and/or lower eyelid fat pads in the periorbital region of the subject; assessing the one or more upper and/or lower eyelid fat pads at a predetermined amount of time after the administration of the composition; determining whether there is an improvement in the periorbital puffiness; and optionally surgically resecting a portion of one or more of upper and/or lower eyelid fat pads where there is no improvement in periorbital puffiness after administration of the composition.

In some embodiments of each or any of the above- or below-mentioned embodiments, the protein having hyaluronidase activity is hyaluronidase.

The present disclosure also provides methods of treating periorbital puffiness in a subject in need thereof by determining if the periorbital puffiness is due to edema or a structural change; and administering a protein having hyaluronidase activity to the periorbital region of the subject if the periorbital puffiness is due to edema.

In some embodiments of each or any of the above- or below-mentioned embodiments, the determining step comprises: administering a first dose of a composition that comprises a protein having hyaluronidase activity to a periorbital region of the subject; assessing the periorbital region at a predetermined amount of time after the administration of the composition; and determining whether there is an improvement in the periorbital puffiness.

In some embodiments of each or any of the above- or below-mentioned embodiments, the structural change is a herniation of an eyelid fat pad.

In some embodiments of each or any of the above- or below-mentioned embodiments, the predetermined time is 5 minutes, 15 minutes, 30 minutes, 1 hour, 24 hours, or 1 week after administration of the composition.

In some embodiments of each or any of the above- or below-mentioned embodiments, no improvement in periorbital puffiness indicates that the periorbital puffiness is due to a structural change.

In some embodiments of each or any of the above- or below-mentioned embodiments, a partial improvement in periorbital puffiness indicates that the periorbital puffiness is secondary to both edema and a structural change.

In some embodiments of each or any of the above- or below-mentioned embodiments, an improvement in periorbital puffiness indicates that the periorbital puffiness is secondary to edema.

In some embodiments of each or any of the above- or below-mentioned embodiments, an improvement includes a reduction in the periorbital puffiness.

In some embodiments of each or any of the above- or below-mentioned embodiments, the protein having hyaluronidase activity is hyaluronidase.

In some embodiments of each or any of the above- or below-mentioned embodiments, the hyaluronidase is a recombinant hyaluronidase.

In some embodiments of each or any of the above- or below-mentioned embodiments, the step of administering is performed by one or more injections into one or more upper and/or lower eyelid fat pads.

In some embodiments of each or any of the above- or below-mentioned embodiments, each injection includes about 1 to about 1,000 Units of the protein having hyaluronidase activity.

The present disclosure also provides methods for treating a subject with periorbital puffiness by determining if periorbital puffiness is due to edema or a structural change in the subject; administering a protein having hyaluronidase activity to the periorbital region of the subject where the periorbital puffiness is due to edema; and optionally surgically resecting a portion of one or more of the upper and/or lower eyelid fat pads.

Also provided are methods for treating a subject with periorbital puffiness by determining if periorbital puffiness is due to edema or a structural change in the subject; and surgically resecting a portion of one or more of the upper and/or lower eyelid fat pads where the periorbital puffiness is due to a structural change.

In some embodiments of each or any of the above- or below-mentioned embodiments, the protein having hyaluronidase activity is hyaluronidase.

In some embodiments of each or any of the above- or below-mentioned embodiments, the hyaluronidase is a recombinant hyaluronidase.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

FIGS. 5A-5H show a patient seated in the Frankfort horizontal plane with eye puffiness before (Panel A; Aug. 15, 2019) and approximately 1 month after (Panel B; Sep. 4, 2019) subcutaneous injections of a total of 40 U of HYLENEX to four injection sites including: the medial, central and lateral aspects of each of the lower eyelids and the lateral aspect of each of the upper eyelids (10 U per site). Panels C-H provide magnified images of the patients' eyes before (Panels C, E, and G) and after (Panels D, F, and H) treatment with HYLENEX. Panels C and D depict a magnified view of the patient's right eye before and after treatment with HYLENEX, respectively, while asked to look straight ahead level to the ground. Panels E and F depict a magnified view of the patient's right eye before and after treatment with HYLENEX, respectively, while asked to look upwards while maintaining her head in the Frankfort horizontal plane. Panels G and H depict a magnified view of the patient's left eye before and after treatment with HYLENEX, respectively, while asked to look upwards while maintaining her head in the Frankfort horizontal plane.

DETAILED DESCRIPTION

Figure 1A:
FIGS. 1A-1B show a patient seated in the Frankfort horizontal plane with eye puffiness before (Panel A) and 3 months after (Panel B) subcutaneous injections of a total of 40 U of HYLENEX to four injection sites including: the medial, central and lateral aspects of each of the lower eyelids and the lateral aspect of each of the upper eyelids (10 U per site).

It is estimated that at least 32 million Americans over twenty-five years of age suffer from periorbital puffiness or bags around their eyes. This condition is generally attributed to pseudoherniation of one or more of the fat pads located around their eyes. Consequently, these patients often undergo a surgical blepharoplasty procedure to lessen their extent of fullness or bags by removing and/or repositioning the fat pads located around the eyes. However, many patients with periorbital puffiness or bags do not have pseudoherniation of the fat pads located around their eyes. Instead, the puffiness or bags are due to swelling (edema) of the tissues in that region. Given that puffiness may be due to edema and/or a structural change (e.g., pseudoherniation of one or more fat pads) in the periorbital region there exists a need accurately identify the etiology of the puffiness since unnecessary surgery is both costly and may lead to unintended side effects including, a patient exhibiting hollowness in the periorbital region. The inventors have developed a protocol that permits a targeted intervention of periorbital puffiness by identifying whether it is due to edema and/or a structural change. Advantageously, such methods may be used to select an appropriate treatment regimen for patients that exhibit periorbital puffiness.

The present disclosure provides methods for determining if periorbital puffiness in a subject in need thereof is due to edema or a structural change (e.g., a herniation of one or more of the eyelid fats pads located in the periorbital region).

The determination of whether the periorbital puffiness is due to edema or a structural change may be determined by any of the methods disclosed herein. Such methods may include administering a composition that comprises a protein having hyaluronidase activity to a periorbital region of the subject, assessing the periorbital region at a predetermined amount of time after the administration of the composition, and determining whether there is an improvement in the periorbital puffiness (e.g., a decrease in the puffiness including, for example, a visible decrease in puffiness). Such methods may be performed to determine if a subject is a candidate for treatment with a protein having hyaluronidase activity. For example, if the subject exhibits an improvement or a partial improvement in periorbital puffiness, the subject is considered a candidate for treatment with the protein having hyaluronidase activity. Alternatively, if the subject does not exhibit an improvement in periorbital puffiness, the subject is not considered a candidate for treatment with the protein having hyaluronidase activity. Instead, such a subject is considered a candidate for a blepharoplasty (e.g., the removal of all or a portion of one or more periorbital fat pads). In an embodiment where a subject is determined to be a candidate for such treatment, the subject is subsequently treated with the protein having hyaluronidase activity in one or more treatment sessions including treatment sessions that are 1 week, 2 weeks, 3 weeks, 1 month, 2 months, 3 months, 4 months, 5 months, or 6 months apart.

In an embodiment, a subject may be administered an initial dose of the composition comprising the protein having hyaluronidase activity and then treated with a second dose of the same composition where the periorbital puffiness exhibits an improvement (e.g., a reduction in periorbital puffiness) after administration of the first dose. If the puffiness does not improve, it is due to a structural change and the subject is not treated with the composition comprising the protein having hyaluronidase activity.

In an embodiment, the periorbital puffiness is unrelated to a use of a hyaluronic acid filler in the periorbital region.

The present disclosure also provides methods of determining if periorbital puffiness is due to edema or a structural change in a subject by administering a composition that comprises a protein having hyaluronidase activity to the periorbital region of the subject; assessing the periorbital region at a predetermined amount of time after the administration of the composition; and determining whether there is an improvement in the periorbital puffiness.

The present disclosure also provides methods for determining if a subject that exhibits with periorbital puffiness is a candidate for a blepharoplasty by determining if the periorbital puffiness is due to edema or a structural change in a subject, comprising the steps of: administering a composition that comprises a protein having hyaluronidase activity to a periorbital region of the subject; assessing the periorbital region at a predetermined amount of time after the administration of the composition; and determining whether there is an improvement in the periorbital puffiness, wherein the subject is a candidate for a blepharoplasty if there is no improvement in the periorbital puffiness.

As used herein, the term "periorbital puffiness" also known as swelling or fullness around the eyes is the appearance of swelling in the tissues around the eyes, called the orbits. It may be caused by fluid buildup around the eyes, or periorbital edema including edema in the peri-orbital fat pads and soft tissues. Periorbital puffiness may also be due to swelling or fullness of the malar region.

As used herein, "hyaluronidase" refers to an enzyme that degrades hyaluronic acid. Hyaluronidases include bacterial hyaluronidases (EC 4.2.99.1), hyaluronidases from leeches, spiders, snakes, parasites, and crustaceans (EC 3.2.1.36), and mammalian-type hyaluronidases (EC 3.2.1.35). Hyaluronidases also include any of non-human origin including, but not limited to, murine, canine, feline, leporine, avian, bovine, ovine, porcine, equine, piscine, ranine, bacterial, and any from leeches, other parasites, and crustaceans. Hyaluronidases also include those of human origin. Also included amongst hyaluronidases are soluble hyaluronidases.

Reference to hyaluronidases includes precursor hyaluronidase polypeptides and mature hyaluronidase polypeptides (such as those in which a signal sequence has been removed), truncated forms thereof that have activity, and includes allelic variants and species variants, variants encoded by splice variants, and other variants. Hyaluronidases also include those that contain chemical or posttranslational modifications and those that do not contain chemical or posttranslational modifications. Such modifications include, but are not limited to, pegylation, albumination, glycosylation, farnesylation, carboxylation, hydroxylation, phosphorylation, and other polypeptide modifications known in the art.

As used herein, a soluble hyaluronidase refers to a polypeptide characterized by its solubility under physiologic conditions. Soluble hyaluronidases can be distinguished, for example, by its partitioning into the aqueous phase of a Triton X-114 solution warmed to 37° C. (Bordier et al., (1981) J. Biol. Chem., 256:1604-7). Membrane-anchored, such as lipid anchored hyaluronidases, will partition into the detergent rich phase, but will partition into the detergent-poor or aqueous phase following treatment with Phospholipase-C. Included among soluble hyaluronidases are membrane anchored hyaluronidases in which one or more regions associated with anchoring of the hyaluronidase to the membrane has been removed or modified, where the soluble form retains hyaluronidase activity. Soluble hyaluronidases include recombinant soluble hyaluronidases and those contained in or purified from natural sources, such as, for example, testes extracts from sheep or cows.

As used herein, "hyaluronidase activity" refers to the ability of a protein to cleave hyaluronic acid. In vitro assays to determine the hyaluronidase activity of hyaluronidases are known in the art and described herein. Exemplary assays include the microturbidity assay that measures cleavage of hyaluronic acid by hyaluronidase indirectly by detecting the insoluble precipitate formed when the uncleaved hyaluronic acid binds with serum albumin.

The terms, "treating" or "treatment" of a disease, disorder, or condition includes at least partially: (1) preventing the disease, disorder, or condition, i.e. causing the clinical symptoms of the disease, disorder, or condition not to develop in a mammal that is exposed to or predisposed to the disease, disorder, or condition but does not yet experience or display symptoms of the disease, disorder, or condition; (2) inhibiting the disease, disorder, or condition, i.e., arresting or reducing the development of the disease, disorder, or condition or its clinical symptoms; or (3) relieving the disease, disorder, or condition, i.e., causing regression of the disease, disorder, or condition or its clinical symptoms. The term "treating," includes to reducing any detectable amount or eliminating in an individual puffiness. In some embodiments, puffiness may be reduced at least about 20%, at least about 30%, at least about 40%, at least about 50%, at least about 60%, at least about 70%, at least about 80%, at least about 90% or at least about 100%.

The terms "prevention", "prevent", "preventing", "suppression", "suppress", "suppressing", "inhibit" and "inhibition" as used herein refer to a course of action initiated in a manner so as to prevent, suppress or reduce, either temporarily or permanently, the onset of a clinical manifestation of the disease state or condition. Such preventing, suppressing or reducing need not be absolute to be useful.

The terms "improvement" or "improving" as used herein in reference to periorbital puffiness refers to a reduction in periorbital puffiness.

The terms "reducing" or "reduction" as used herein refers to a decrease (or lowering) in the amount, mass, and/or volume of periorbital puffiness. Such reduction can be measured and determined by measuring the amount of puffiness according to one or more of the methods described herein including, for example, at an initial time point prior to the administering of the compounds described herein and then measuring the amount of puffiness at various time points (e.g. during the period of administering the compounds described herein as well after the administering has ceased). For example, a subject's puffiness can be measured prior to beginning a treatment regimen with the compounds described herein and then measured during and after the treatment regimen. A decrease in puffiness is indicative of a reduction in puffiness. Additionally, the reduction of puffiness can be determined qualitatively such as by photographing the face or eyes, at various time points before, during, and after a treatment regimen where the reduction in puffiness can be determined by visual inspection of the images. A reduction in puffiness includes, for example, a 30%, 35%, 40%, 45%, 50%, 55%, 60%, 65%, 70%, 75%, 80%, 85%, 90%, 95%, 100%, or greater lowering or decrease in the amount, mass, and/or volume of periorbital puffiness. Alternatively, a subject's puffiness is given a score of 10 (on a scale of 1 to 10 with 1 being no periorbital puffiness) prior to treatment with the composition disclosed herein. The subject and/or medical practitioner that administered the composition then scores the puffiness after treatment with a subjective grade based on the original score of 10 (e.g., the score is given based on a visual assessment of the subject from a before photograph of the periorbital puffiness). A decrease in puffiness measured as a score of 6 or less indicates a reduction in periorbital puffiness. Alternatively, a reduction in puffiness may be determined by a reduction in in a PFAS grade (e.g., a score of L 0/3E [left eye; upper eyelid over lower eyelid] and a R 0/3E [right eye; upper eyelid over lower eyelid] to a score of L 0/1E and L 0/1E). A reduction in PFAS grade corresponds to a reduction in the Grade number (e.g., a 3 to a 2).

The terms "partially improve" or "partial improvement" as used herein in reference to periorbital puffiness refers to a small (or minor) reduction in periorbital puffiness such as a 5%, 10%, 15%, 20%, or 25% lowering or decrease in the amount, mass, and/or volume of puffiness. Alternatively, a subject's puffiness is given a score of 10 (on a scale of 1 to 10 with 1 being no periorbital puffiness) prior to treatment with the composition disclosed herein. The subject and/or medical practitioner that administered the composition then scores the puffiness after treatment with a subjective grade based on the original score of 10 (e.g., the score is given based on a visual assessment of the subject from a before photograph of the periorbital puffiness). A decrease in puffiness measured as a score of 7 to 9 indicates a partial improvement in periorbital puffiness.

The terms "worsens" or "worse" as used herein in reference to periorbital puffiness refer to an increase in periorbital puffiness.

The terms "increased" or "increase" as used herein refers to an increase in the amount, mass, and/or volume of periorbital puffiness. Such increase can be measured and determined by measuring the amount of puffiness according to one or more of the methods described herein including, for example, at an initial time point prior to the administering of the compounds described herein and then measuring the amount of puffiness at various time points (e.g. during the period of administering the compounds described herein as well after the administering has ceased). For example, a subject's puffiness can be measured prior to beginning a treatment regimen with the compounds described herein and then measured during and after the treatment regimen. Additionally, the increase in puffiness can be determined qualitatively such as by photographing the face or eyes including, for example, at various time points before, during, and after a treatment regimen where the reduction in puffiness can be determined by visual inspection of the images. An increase in puffiness incudes, for example, a 5%, 10%, 15%, 20%, 25%, 30%, 35%, 40%, 45%, 50%, 55%, 60%, 65%, 70%, 75%, 80%, 85%, 90%, 95%, 100%, or increase in the amount, mass, and/or volume of periorbital puffiness. Alternatively, an increase in puffiness may be determined by an increase in a PFAS grade (e.g., a score of L 0/1E [left eye; upper eyelid over lower eyelid] and a R 0/1E [right eye; upper eyelid over lower eyelid] to a score of L 0/3E and L 0/3E). A increase in PFAS grade corresponds to an increase in the Grade number (e.g., a 1 to a 3).

As used herein, the term "subject" refers to an animal, including a mammal, such as a human being.

As used herein, a patient refers to a human subject.

As used herein, amelioration of the symptoms by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, prevention or prophylaxis refers to methods in which the risk of developing disease or condition is reduced.

As used herein, a "therapeutically effective amount" or a "therapeutically effective dose" refers to the quantity of an agent, compound, material, or composition containing a compound that is at least sufficient to produce a therapeutic effect. Hence, it is the quantity necessary for preventing, curing, ameliorating, arresting or partially arresting a symptom of a disease, disorder, or condition.

As used herein, the singular forms "a," "an" and "the" include plural referents unless the context clearly dictates otherwise. Thus, for example, reference to a compound, comprising "an extracellular domain" includes compounds with one or a plurality of extracellular domains.

As used herein, ranges and amounts can be expressed as "about" a particular value or range. About also includes the exact amount. Hence "about 5 bases" means "about 5 bases" and also "5 bases."

Hyaluronidase

Hyaluronidases are a family of enzymes that degrade hyaluronic acid. There are three general classes of hyaluronidases; mammalian hyaluronidase, bacterial hyaluronidase and hyaluronidase from leeches, other parasites and crustaceans. Mammalian-type hyaluronidases (EC 3.2.1.35) are endo-β-N-acetyl-hexosaminidases that hydrolyze the β1→4 glycosidic bond of hyaluronan into various oligosaccharide lengths such as tetrasaccharides and hexasaccharides. They have both hydrolytic and transglycosidase activities, and can degrade hyaluronan and chondroitin sulfates (CS), generally C4-S and C6-S. Hyaluronidases of this type include, but are not limited to, hyaluronidases from cows (bovine), mouse, pig, rat, rabbit, sheep (ovine), orangutan, cynomolgus monkey, guinea pig, and human hyaluronidases.

Mammalian hyaluronidases can be further subdivided into those that are neutral active, predominantly found in testes extracts, and acid active, predominantly found in organs such as the liver. Exemplary neutral active hyaluronidases include PH20. Human PH20 (also known as SPAM1 or sperm surface protein PH20), is generally locked to the plasma membrane via a glycosylphosphatidyl inositol (GPI) anchor. It is naturally involved in sperm-egg adhesion and aids penetration by sperm of the layer of cumulus cells by digesting hyaluronic acid. Alignment of bovine PH20 with the human PH20 shows only weak homology, with multiple gaps existing from amino acid 470 through to the respective carboxy termini due to the absence of a GPI anchor in the bovine polypeptide (see e.g., Frost GI (2007) Expert Opin. Drug. Deliv. 4: 427-440). In fact, no clear GPI anchor is predicted in any other PH20 species besides humans. Thus, PH20 polypeptides produced from ovine and bovine exist as soluble forms. Though bovine PH20 exists very loosely attached to the plasma membrane, it is not anchored via a phospholipase sensitive anchor (Lalancette et al, Biol Reprod. 2001 August; 65(2):628-36). This unique feature of bovine hyaluronidase has permitted the use of the soluble bovine testes hyaluronidase enzyme as an extract for clinical use (Wydase™, Hyalase™).

Besides human PH20 (also termed SPAM1), five hyaluronidase-like genes have been identified in the human genome, HYAL1, HYAL2, HYAL3, HYAL4 and HYALP1. HYALP1 is a pseudogene, and HYAL3 has not been shown to possess enzyme activity toward any known substrates. The hyaluronidase-like enzymes can also be characterized by those which are generally locked to the plasma membrane via a glycosylphosphatidyl inositol anchor such as human HYAL2 and human PH20 (Danilkovitch-Miagkova, et al. (2003) Proc Natl Acad Sci USA. 100(8):4580-5), and those which are generally soluble such as human HYAL1 (Frost et al, (1997) Biochem Biophys Res Commun. 236 (1):10-5).

In a preferred embodiment, the hyaluronidase is HYLENEX (having the amino acid sequence as set forth in SEQ ID NO: 1).

Glycosylation, including N- and O-linked glycosylation, of some hyaluronidases can be very important for their catalytic activity and stability. While altering the type of glycan modifying a glycoprotein can have dramatic effects on a protein's antigenicity, structural folding, solubility, and stability, most enzymes are not thought to require glycosylation for optimal enzyme activity. Such hyaluronidases are unique in this regard, in that removal of N-linked glycosylation can result in near complete inactivation of the hyaluronidase activity. For such hyaluronidases, the presence of N-linked glycans is critical for generating an active enzyme.

N-linked oligosaccharides fall into several major types (oligomannose, complex, hybrid, sulfated), all of which have (Man) 3-GlcNAc-GlcNAc-cores attached via the amide nitrogen of Asn residues that fall within-Asn-Xaa-Thr/Ser-sequences (where Xaa is not Pro). Glycosylation at an -Asn-Xaa-Cys-site has been reported for coagulation protein C. In some instances, the hyaluronidase can contain both N-glycosidic and O-glycosidic linkages.

Soluble hyaluronidases include any that exist in soluble form, including, but not limited to, Hyal1, bovine PH20 and ovine PH20, allelic variants thereof and other variants. Also included among soluble hyaluronidase are any hyaluronidase that has been modified to be soluble. For example, human PH20, which is normally membrane anchored via a GPI anchor, can be made soluble by truncation of and removal of all or a portion of the GPI anchor at the C-terminus. Soluble hyaluronidases also include neutral active and acid active hyaluronidases, however, neutral active hyaluronidases are contemplated for use herein for purposes of subcutaneous administration.

Polypeptides of a soluble hyaluronidase set forth herein, can be obtained by methods well known in the art for protein purification and recombinant protein expression. Any method known to those of skill in the art for identification of nucleic acids that encode desired genes can be used. Any method available in the art can be used to obtain a full length (i.e., encompassing the entire coding region) cDNA or genomic DNA clone encoding a hyaluronidase, such as from a cell or tissue source. Modified or variant soluble hyaluronidases, can be engineered from a wild type polypeptide, such as by site-directed mutagenesis.

Polypeptides can be cloned or isolated using any available methods known in the art for cloning and isolating nucleic acid molecules. Such methods include PCR amplification of nucleic acids and screening of libraries, including nucleic acid hybridization screening, antibody-based screening and activity-based screening.

Methods for amplification of nucleic acids can be used to isolate nucleic acid molecules encoding a desired polypeptide, including for example, polymerase chain reaction (PCR) methods. A nucleic acid containing material can be used as a starting material from which a desired polypeptide-encoding nucleic acid molecule can be isolated. For example, DNA and mRNA preparations, cell extracts, tissue extracts, fluid samples (e.g. blood, serum, saliva), samples from healthy and/or diseased subjects can be used in amplification methods. Nucleic acid libraries also can be used as a source of starting material. Primers can be designed to amplify a desired polypeptide. For example, primers can be designed based on expressed sequences from which a desired polypeptide is generated. Primers can be designed based on back-translation of a polypeptide amino acid sequence. Nucleic acid molecules generated by amplification can be sequenced and confirmed to encode a desired polypeptide.

Additional nucleotide sequences can be joined to a polypeptide-encoding nucleic acid molecule, including linker sequences containing restriction endonuclease sites for the purpose of cloning the synthetic gene into a vector, for example, a protein expression vector or a vector designed for the amplification of the core protein coding DNA sequences. Furthermore, additional nucleotide sequences specifying functional DNA elements can be operatively linked to a polypeptide-encoding nucleic acid molecule. Examples of such sequences include, but are not limited to, promoter sequences designed to facilitate intracellular protein expression, and secretion sequences, for example heterologous signal sequences, designed to facilitate protein secretion. Such sequences are known to those of skill in the art. Additional nucleotide residues sequences such as sequences of bases specifying protein binding regions also can be linked to enzyme-encoding nucleic acid molecules. Such regions include, but are not limited to, sequences of residues that facilitate or encode proteins that facilitate uptake of an enzyme into specific target cells, or otherwise alter pharmacokinetics of a product of a synthetic gene. For example, enzymes can be linked to PEG moieties.

In addition, tags or other moieties can be added, for example, to aid in detection or affinity purification of the polypeptide. For example, additional nucleotide residues sequences such as sequences of bases specifying an epitope tag or other detectable marker also can be linked to enzyme-encoding nucleic acid molecules. Exemplary of such sequences include nucleic acid sequences encoding a His tag (e.g., 6×His) or Flag Tag.

The identified and isolated nucleic acids can then be inserted into an appropriate cloning vector. A large number of vector-host systems known in the art can be used. Possible vectors include, but are not limited to, plasmids or modified viruses, but the vector system must be compatible with the host cell used. Such vectors include, but are not limited to, bacteriophages such as lambda derivatives, or plasmids such as pCMV4, pBR322 or pUC plasmid derivatives or the Bluescript vector (Stratagene, La Jolla, Calif.).

Other expression vectors include the HZ24 expression vector exemplified herein. The insertion into a cloning vector can, for example, be accomplished by ligating the DNA fragment into a cloning vector which has complementary cohesive termini. Insertion can be effected using TOPO cloning vectors (INVITROGEN, Carlsbad, Calif.). If the complementary restriction sites used to fragment the DNA are not present in the cloning vector, the ends of the DNA molecules can be enzymatically modified. Alternatively, any site desired can be produced by ligating nucleotide sequences (linkers) onto the DNA termini; these ligated linkers can contain specific chemically synthesized oligonucleotides encoding restriction endonuclease recognition sequences. In an alternative method, the cleaved vector and protein gene can be modified by homopolymeric tailing. Recombinant molecules can be introduced into host cells via, for example, transformation, transfection, infection, electroporation and sonoporation, so that many copies of the gene sequence are generated.

In specific embodiments, transformation of host cells with recombinant DNA molecules that incorporate the isolated protein gene, cDNA, or synthesized DNA sequence enables generation of multiple copies of the gene. Thus, the gene can be obtained in large quantities by growing transformants, isolating the recombinant DNA molecules from the transformants and, when necessary, retrieving the inserted gene from the isolated recombinant DNA.

For recombinant expression of one or more of the desired proteins, such as any described herein, the nucleic acid containing all or a portion of the nucleotide sequence encoding the protein can be inserted into an appropriate expression vector, i.e., a vector that contains the necessary elements for the transcription and translation of the inserted protein coding sequence. The necessary transcriptional and translational signals also can be supplied by the native promoter for enzyme genes, and/or their flanking regions.

Also provided are vectors that contain a nucleic acid encoding the enzyme. Cells containing the vectors also are provided. The cells include eukaryotic and prokaryotic cells, and the vectors are any suitable for use therein.

Prokaryotic and eukaryotic cells, including endothelial cells, containing the vectors are provided. Such cells include bacterial cells, yeast cells, fungal cells, Archea, plant cells, insect cells and animal cells. The cells are used to produce a protein thereof by growing the above-described cells under conditions whereby the encoded protein is expressed by the cell, and recovering the expressed protein. For purposes herein, for example, the enzyme can be secreted into the medium.

Also provided are vectors that contain a sequence of nucleotides that encodes the soluble hyaluronidase polypeptide coupled to the native or heterologous signal sequence, as well as multiple copies thereof. The vectors can be selected for expression of the enzyme protein in the cell or such that the enzyme protein is expressed as a secreted protein.

A variety of host-vector systems can be used to express the protein coding sequence. These include but are not limited to mammalian cell systems infected with virus (e.g. vaccinia virus, adenovirus and other viruses); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system used, any one of a number of suitable transcription and translation elements can be used.

Any methods known to those of skill in the art for the insertion of DNA fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid sequences encoding protein, or domains, derivatives, fragments or homologs thereof, can be regulated by a second nucleic acid sequence so that the genes or fragments thereof are expressed in a host transformed with the recombinant DNA molecule(s). For example, expression of the proteins can be controlled by any promoter/enhancer known in the art. In a specific embodiment, the promoter is not native to the genes for a desired protein. Promoters which can be used include but are not limited to the SV40 early promoter (Bernoist and Chambon, Nature 290:304-310 (1981)), the promoter contained in the 3' long terminal repeat of Rous sarcoma virus (Yamamoto et al. Cell 22:787-797 (1980)), the herpes thymidine kinase promoter (Wagner et al., Proc. Natl. Acad. Sci. USA 78:1441-1445 (1981)), the regulatory sequences of the metallothionein gene (Brinster et al., Nature 296:39-42 (1982)); prokaryotic expression vectors such as the β-lactamase promoter (Jay et al., (1981) Proc. Natl. Acad. Sci. USA 78:5543) or the tac promoter (DeBoer et al., Proc. Natl. Acad. Sci. USA 80:21-25 (1983)); see also "Useful Proteins from Recombinant Bacteria": in Scientific American 242:79-94 (1980)); plant expression vectors containing the nopaline synthetase promoter (Herrara-Estrella et al., Nature 303:209-213 (1984)) or the cauliflower mosaic virus 35S RNA promoter (Garder et al., Nucleic Acids Res. 9:2871 (1981)), and the promoter of the photosynthetic enzyme ribulose bisphosphate carboxylase (Herrera-Estrella et al., Nature 310:115-120 (1984)); promoter elements from yeast and other fungi such as the Ga14 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al., Cell 38:639-646 (1984); Ornitz et al., Cold Spring Harbor Symp. Quant. Biol. 50:399-409 (1986); MacDonald, Hepatology 7:425-515 (1987)); insulin gene control region which is active in pancreatic beta cells (Hanahan et al., Nature 315:115-122 (1985)), immunoglobulin gene control region which is active in lymphoid cells (Grosschedl et al., Cell 38:647-658 (1984); Adams et al., Nature 318:533-538 (1985); Alexander et al., Mol. Cell Biol. 7:1436-1444 (1987)), mouse mammary tumor virus control region which is active in testicular, breast, lymphoid and mast cells (Leder et al., Cell 45:485-495 (1986)), albumin gene control region which is active in liver (Pinckert et al., Genes and Devel. 1:268-276 (1987)), alpha-fetoprotein gene control region which is active in liver (Krumlauf et al., Mol. Cell. Biol. 5:1639-1648 (1985); Hammer et al., Science 235:53-58 1987)), alpha-1 antitrypsin gene control region which is active in liver (Kelsey et al., Genes and Devel. 1:161-171 (1987)), beta globin gene control region which is active in myeloid cells (Magram et al., Nature 315:338-340 (1985); Kollias et al., Cell 46:89-94 (1986)), myelin basic protein gene control region which is active in oligodendrocyte cells of the brain (Readhead et al., Cell 48:703-712 (1987)), myosin light chain-2 gene control region which is active in skeletal muscle (Shani, Nature 314:283-286 (1985)), and gonadotrophic releasing hormone gene control region which is active in gonadotrophs of the hypothalamus (Mason et al., Science 234:1372-1378 (1986)).

In a specific embodiment, a vector is used that contains a promoter operably linked to nucleic acids encoding a desired protein, or a domain, fragment, derivative or homolog, thereof, one or more origins of replication, and optionally, one or more selectable markers (e.g., an antibiotic resistance gene). Exemplary plasmid vectors for transformation of E. coli cells, include, for example, the pQE expression vectors (available from Qiagen, Valencia, Calif.; see also literature published by Qiagen describing the system). pQE vectors have a phage T5 promoter (recognized by E. coli RNA polymerase) and a double lac operator repression module to provide tightly regulated, high-level expression of recombinant proteins in E. coli, a synthetic ribosomal binding site (RBS II) for efficient translation, a 6×His tag coding sequence, t0 and T1 transcriptional terminators, ColE1 origin of replication, and a beta-lactamase gene for conferring ampicillin resistance. The pQE vectors enable placement of a 6×His tag at either the N- or C-terminus of the recombinant protein. Such plasm ids include pQE 32, pQE 30, and pQE 31 which provide multiple cloning sites for all three reading frames and provide for the expression of N-terminally 6×His-tagged proteins. Other exemplary plasmid vectors for transformation of E. coli cells, include, for example, the pET expression vectors (see, U.S. Pat. No. 4,952,496; available from NOVAGEN, Madison, Wis.; see, also literature published by Novagen describing the system). Such plasmids include pET 11 a, which contains the T7lac promoter, T7 terminator, the inducible E. coli lac operator, and the lac repressor gene; pET 12a-c, which contains the T7 promoter, T7 terminator, and the E. coli ompT secretion signal; and pET 15b and pET19b (NOVAGEN, Madison, Wis.), which contain a His-Tag™ leader sequence for use in purification with a His column and a thrombin cleavage site that permits cleavage following purification over the column, the T7-lac promoter region and the T7 terminator.

Soluble hyaluronidase polypeptides can be produced by any method known to those of skill in the art including in vivo and in vitro methods. Desired proteins can be expressed in any organism suitable to produce the required amounts and forms of the proteins, such as for example, needed for administration and treatment. Expression hosts include prokaryotic and eukaryotic organisms such as E. coli, yeast, plants, insect cells, mammalian cells, including human cell lines and transgenic animals. Expression hosts can differ in their protein production levels as well as the types of post-translational modifications that are present on the expressed proteins. The choice of expression host can be made based on these and other factors, such as regulatory and safety considerations, production costs and the need and methods for purification.

Many expression vectors are available and known to those of skill in the art and can be used for expression of proteins. The choice of expression vector will be influenced by the choice of host expression system. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vector.

Soluble hyaluronidase polypeptides also can be utilized or expressed as protein fusions. For example, an enzyme fusion can be generated to add additional functionality to an enzyme. Examples of enzyme fusion proteins include, but are not limited to, fusions of a signal sequence, a tag such as for localization, e.g. a his6 tag or a myc tag, or a tag for purification, for example, a GST fusion, and a sequence for directing protein secretion and/or membrane association.

Prokaryotes, especially E. coli, provide a system for producing large amounts of proteins. Transformation of E. coli is simple and rapid technique well known to those of skill in the art. Expression vectors for E. coli can contain inducible promoters, such promoters are useful for inducing high levels of protein expression and for expressing proteins that exhibit some toxicity to the host cells. Examples of inducible promoters include the lac promoter, the trp promoter, the hybrid tac promoter, the T7 and SP6 RNA promoters and the temperature regulated APL promoter.

Proteins, such as any provided herein, can be expressed in the cytoplasmic environment of E. coli. The cytoplasm is a reducing environment and for some molecules, this can result in the formation of insoluble inclusion bodies. Reducing agents such as dithiothreitol and β-mercaptoethanol and denaturants, such as guanidine-HCl and urea can be used to resolubilize the proteins. An alternative approach is the expression of proteins in the periplasmic space of bacteria which provides an oxidizing environment and chaperoninlike and disulfide isomerases and can lead to the production of soluble protein. Typically, a leader sequence is fused to the protein to be expressed which directs the protein to the periplasm. The leader is then removed by signal peptidases inside the periplasm. Examples of periplasmic-targeting leader sequences include the pelB leader from the pectate lyase gene and the leader derived from the alkaline phosphatase gene. In some cases, periplasmic expression allows leakage of the expressed protein into the culture medium. The secretion of proteins allows quick and simple purification from the culture supernatant. Proteins that are not secreted can be obtained from the periplasm by osmotic lysis. Similar to cytoplasmic expression, in some cases proteins can become insoluble and denaturants and reducing agents can be used to facilitate solubilization and refolding. Temperature of induction and growth also can influence expression levels and solubility, typically temperatures between 25° C. and 37° C. are used. Typically, bacteria produce aglycosylated proteins. Thus, if proteins require glycosylation for function, glycosylation can be added in vitro after purification from host cells.

Yeasts such as *Saccharomyces cerevisae, Schizosaccharomyces pombe, Yarrowia lipolytica, Kluyveromyces lactis* and *Pichia pastoris* are well known yeast expression hosts that can be used for production of proteins, such as any described herein. Yeast can be transformed with episomal replicating vectors or by stable chromosomal integration by homologous recombination. Typically, inducible promoters are used to regulate gene expression. Examples of such promoters include GAL1, GALT and GALS and metallothionein promoters, such as CUP1, AOX1 or other *Pichia* or other yeast promoter. Expression vectors often include a selectable marker such as LEU2, TRP1, HIS3 and URA3 for selection and maintenance of the transformed DNA. Proteins expressed in yeast are often soluble. Co-expression with chaperonins such as Bip and protein disulfide isomerase can improve expression levels and solubility. Additionally, proteins expressed in yeast can be directed for secretion using secretion signal peptide fusions such as the yeast mating type alpha-factor secretion signal from *Saccharomyces cerevisae* and fusions with yeast cell surface proteins such as the Aga2p mating adhesion receptor or the *Arxula adeninivorans* glucoamylase. A protease cleavage site such as for the Kex-2 protease, can be engineered to remove the fused sequences from the expressed polypeptides as they exit the secretion pathway. Yeast also is capable of glycosylation at Asn-X-Ser/Thr motifs.

Insect cells, particularly using baculovirus expression, are useful for expressing polypeptides such as hyaluronidase polypeptides. Insect cells express high levels of protein and are capable of most of the post-translational modifications used by higher eukaryotes. Baculovirus have a restrictive host range which improves the safety and reduces regulatory concerns of eukaryotic expression. Typical expression vectors use a promoter for high level expression such as the polyhedrin promoter of baculovirus. Commonly used baculovirus systems include the baculoviruses such as *Autographa californica* nuclear polyhedrosis virus (AcNPV), and the *Bombyx mori* nuclear polyhedrosis virus (BmNPV) and an insect cell line such as Sf9 derived from *Spodoptera frugiperda, Pseudaletia unipuncta* (A7S) and *Danaus plexippus* (DpN1). For high-level expression, the nucleotide sequence of the molecule to be expressed is fused immediately downstream of the polyhedrin initiation codon of the virus. Mammalian secretion signals are accurately processed in insect cells and can be used to secrete the expressed protein into the culture medium. In addition, the cell lines *Pseudaletia unipuncta* (A7S) and *Danaus plexippus* (DpN1) produce proteins with glycosylation patterns similar to mammalian cell systems.

An alternative expression system in insect cells is the use of stably transformed cells. Cell lines such as the Schneider 2 (S2) and Kc cells (*Drosophila melanogaster*) and C7 cells (*Aedes albopictus*) can be used for expression. The *Drosophila* metallothionein promoter can be used to induce high levels of expression in the presence of heavy metal induction with cadmium or copper. Expression vectors are typically maintained by the use of selectable markers such as neomycin and hygromycin.

Mammalian expression systems can be used to express proteins including soluble hyaluronidase polypeptides. Expression constructs can be transferred to mammalian cells by viral infection such as adenovirus or by direct DNA transfer such as liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. IRES elements also can be added to permit bicistronic expression with another gene, such as a selectable marker. Such vectors often include transcriptional promoter-enhancers for high-level expression, for example the SV40 promoter-enhancer, the human cytomegalovirus (CMV) promoter and the long terminal repeat of Rous sarcoma virus (RSV). These promoter-enhancers are active in many cell types. Tissue and cell-type promoters and enhancer regions also can be used for expression.

Exemplary promoter/enhancer regions include, but are not limited to, those from genes such as elastase I, insulin, immunoglobulin, mouse mammary tumor virus, albumin, alpha fetoprotein, alpha 1 antitrypsin, beta globin, myelin basic protein, myosin light chain 2, and gonadotropic releasing hormone gene control. Selectable markers can be used to select for and maintain cells with the expression construct. Examples of selectable marker genes include, but are not limited to, hygromycin B phosphotransferase, adenosine deaminase, xanthine-guanine phosphoribosyl transferase, aminoglycoside phosphotransferase, dihydrofolate reductase (DHFR) and thymidine kinase. For example, expression can be performed in the presence of methotrexate to select for only those cells expressing the DHFR gene. Fusion with cell surface signaling molecules such as TCR-ζ and FcεRI-γ can direct expression of the proteins in an active state on the cell surface.

Many cell lines are available for mammalian expression including mouse, rat human, monkey, chicken and hamster cells. Exemplary cell lines include but are not limited to CHO, Balb/3T3, HeLa, MT2, mouse NSO (nonsecreting) and other myeloma cell lines, hybridoma and heterohybridoma cell lines, lymphocytes, fibroblasts, Sp2/0, COS, NIH3T3, HEK293, 293S, 2B8, and HKB cells. Cell lines also are available adapted to serum-free media which facilitates purification of secreted proteins from the cell culture media. Examples include CHO-S cells (Invitrogen, Carlsbad, Calif., cat #11619-012) and the serum free EBNA-1 cell line (Pham et al., (2003) Biotechnol. Bioeng. 84:332-42). Cell lines also are available that are adapted to grow in special mediums optimized for maximal expression. For example, DG44 CHO cells are adapted to grow in suspension culture in a chemically defined, animal product-free medium.

Method for purification of polypeptides, including soluble hyaluronidase polypeptides or other proteins, from host cells will depend on the chosen host cells and expression systems.

For secreted molecules, proteins are generally purified from the culture media after removing the cells. For intracellular expression, cells can be lysed and the proteins purified from the extract. When transgenic organisms such as transgenic plants and animals are used for expression, tissues or organs can be used as starting material to make a lysed cell extract. Additionally, transgenic animal production can include the production of polypeptides in milk or eggs, which can be collected, and if necessary, the proteins can be extracted and further purified using standard methods in the art.

Proteins, such as soluble hyaluronidase polypeptides, can be purified using standard protein purification techniques known in the art including but not limited to, SDS-PAGE, size fraction and size exclusion chromatography, ammonium sulfate precipitation and ionic exchange chromatography, such as anion exchange. Affinity purification techniques also can be utilized to improve the efficiency and purity of the preparations. For example, antibodies, receptors and other molecules that bind hyaluronidase enzymes can be used in affinity purification. Expression constructs also can be engineered to add an affinity tag to a protein such as a myc epitope, GST fusion or His6 and affinity purified with myc antibody, glutathione resin and Ni-resin, respectively. Purity can be assessed by any method known in the art including gel electrophoresis and staining and spectrophotometric techniques.

Hyaluronidase activity can be assessed using methods well known in the art. In one example, activity is measured using a microturbidity assay. This is based on the formation of an insoluble precipitate when hyaluronic acid binds with serum albumin. The activity is measured by incubating hyaluronidase with sodium hyaluronate (hyaluronic acid) for a set period of time (e.g. 10 minutes) and then precipitating the undigested sodium hyaluronate with the addition of acidified serum albumin. The turbidity of the resulting sample is measured at 640 nm after an additional development period. The decrease in turbidity resulting from hyaluronidase activity on the sodium hyaluronate substrate is a measure of hyaluronidase enzymatic activity. In another example, hyaluronidase activity is measured using a microtiter assay in which residual biotinylated hyaluronic acid is measured following incubation with hyaluronidase (see e.g. Frost and Stern (1997) Anal. Biochem. 251:263-269, U.S. Patent Publication No. 20050260186). The free carboxyl groups on the glucuronic acid residues of hyaluronic acid are biotinylated, and the biotinylated hyaluronic acid substrate is covalently couple to a microtiter plate. Following incubation with hyaluronidase, the residual biotinylated hyaluronic acid substrate is detected using an avidin-peroxidase reaction, and compared to that obtained following reaction with hyaluronidase standards of known activity. Other assays to measure hyaluronidase activity also are known in the art and can be used in the methods herein (see e.g. Delpech et al., (1995) Anal. Biochem. 229:35-41; Takahashi et al., (2003) Anal. Biochem. 322:257-263).

Diagnosing and/or Classifying the Etiology of Periorbital Puffiness

The present disclosure also provides a means to classify the etiology of upper and/or lower eyelid puffiness as caused by localized anatomical changes or systemic etiology leading to inflammatory changes that lead to periorbital puffiness due to periorbital edema. The classification may be used to direct treatment of periorbital puffiness. If the puffiness is secondary to edema, simply removing some of the affected periorbital fat pad(s) will have some initial improvement but will most likely lead to hollowness when the edema in the remaining portion of the fat pad(s) diminishes. When the puffiness is due to the protruding fat pad(s) that has herniated forward in the orbit, then removing part of it is the appropriate course of action. If the etiology of the puffiness is edema of the fat pad(s) or edema of the soft tissue in the eyelids, then treatment should be aimed to decrease the edema in these structures and not to remove part of the fat pad(s).

The Periorbital and Eyelid Fullness Assessment Scale (PPEFAS) defines the etiology of the upper eyelid fullness, lower eyelid fullness, festoons and malar edema to determine the best and safest course of treatment. It determines whether the fullness is secondary to pseudoherniation of the upper and/or lower eyelid fat pads, secondary to edema of the eyelid soft tissues, secondary to edema of the fat pads, or secondary to a combination of pseudoherniation of the fat pads with edema of the fat pads, and/or edema of the peri-orbital soft tissues. The PPEFAS score is represented as the findings in the right upper eyelid/the findings in the lower eyelid and the findings in the left upper eyelid/the findings in the lower eyelid. For example, a patient with pseudoherniation of the medial upper eyelid fat pads bilaterally without any edema of the upper eyelids, edema of the right lower eyelid region without pseudoherniation of the fat pads, and edema with pseudoherniation of the 3 left lower eyelid fat pads would have an PEFAS score of R: 1/0E and L: 1/3E. Thus, the PEFAS score provides a listing the number of herniated fat pads first (1, 2, or 3), anatomical reasons for festoons and malar fullness, if present, (+), and presence of edema last (E).

| Periorbital and Eyelid Fullness Assessment Scale (PEFAS) | |
| --- | --- |
| Grade 0 | No pseudoherniation of the upper and/or lower eyelid fat pads and no associated peri-orbital, malar or eyelid edema |
| Grade 0E | No pseudoherniation of the eyelid fat pads, and one or more of the following:<br>    i. presence of edema of the eyelid fat pads;<br>    ii. presence of edema along the soft tissue of the upper or lower eyelids;<br>    iii. presence of malar mounds due to edema;<br>    iv. presence of malar edema;<br>    v. presence of festoons aggravated by edema |
| Grade 1 | Pseudoherniation of only one of the eyelid fat pads without any associated periorbital, malar and/or eyelid edema |
| Grade 1E | Pseudoherniation of only one of the eyelid fat, and one or more of the following:<br>    i. presence of edema of the fat pad;<br>    ii. presence of edema along the soft tissue of the upper or lower eyelids;<br>    iii. presence of malar mounds due to edema;<br>    iv. presence of malar edema;<br>    v. presence of festoons aggravated by edema |
| Grade 2 | Pseudoherniation of only two of the eyelid fat pads without any associated periorbital, malar and/or eyelid edema |
| Grade 2E | Pseudoherniation of only two of the eyelid fat pads, and one or more of the following:<br>    i. presence of edema of one or more of the fat pads;<br>    ii. presence of edema along the soft tissue of the upper or lower eyelids;<br>    iii. presence of malar mounds due to edema;<br>    iv. presence of malar edema;<br>    v. presence of festoons aggravated by edema |
| Grade 3 | Pseudoherniation of the three lower eyelid fat pads without any associated periorbital, malar and/or eyelid edema |
| Grade 3E | Pseudoherniation of the three lower eyelid fat pads, and one or more of the following:<br>    i. presence of edema of one or more of the lower fat pads;<br>    ii. presence of edema along the soft tissue of the upper or lower eyelids;<br>    iii. presence of malar mounds aggravated by edema; |

| Periorbital and Eyelid Fullness Assessment Scale (PEFAS) | |
|---|---|
| | iv. presence of malar edema;<br>v. presence of festoons aggravated by edema |
| Grade 3+ | Pseudoherniation of the three lower eyelid fat pads with moderate to severe festoons and/or malar mounds secondary to fat deposition or descent/hypertrophy of the orbicularis oculi muscle, and without any associated periorbital, malar or eyelid edema |
| Grade 3+E | Pseudoherniation of the three lower eyelid fat pads with moderate to severe festoons and/or malar mounds secondary to fat deposition or descent/hypertrophy of the orbicularis oculi muscle with one or more of the following:<br>i. presence of edema of one or more of the fat pads;<br>ii. presence of edema along the soft tissue of the upper or lower eyelids;<br>iii. presence of malar mounds aggravated by edema;<br>iv. presence of localized malar edema;<br>v. presence of festoons aggravated by edema |

In an embodiment, a subject is scored as Grade 0 where the subject does not exhibit pseudoherniation of the upper or lower eyelid fat pads and does not exhibit any associated peri-orbital, malar or eyelid edema. In a further embodiment, a subject is scored as Grade 0E where the subject does not exhibit pseudoherniation of any of the upper or lower periorbital fat pads but does exhibit one or more of the following: presence of edema of the upper/lower fat pads, presence of edema along the soft tissue of the upper and/or lower eyelids, presence of malar mounds due to edema, presence of malar edema, and presence of mild festoons aggravated by edema.

In another embodiment, a subject is scored as Grade 1 where the subject exhibits pseudoherniation of only one of the eyelid fat pads (e.g., the upper eyelid medial or central fat pad and/or the lower eyelid medial, central or lateral fat pad) without any associated periorbital, malar and/or eyelid edema.

In yet another embodiment, a subject is scored as Grade 1E where the subject exhibits pseudoherniation of one of the eyelid fat pads (e.g., the upper eyelid medial or central fat pad and/or the lower eyelid medial, central or lateral fat pad), and one or more of the following: presence of edema of the fat pad, presence of edema along the soft tissue of the upper and/or lower eyelids, presence of malar mounds due to edema, presence of malar edema, and presence of mild festoons aggravated by edema.

In another embodiment, a subject is scored as Grade 2 where the subject exhibits pseudoherniation of only two eyelid fat pads (e.g., the upper eyelid medial or central fat pad and/or the lower eyelid medial, central or lateral fat pad) without any associated periorbital, malar and/or eyelid edema.

In yet another embodiment, a subject is scored as Grade 2E where the subject exhibits pseudoherniation of only two eyelid fat pads (e.g., the upper eyelid medial or central fat pad and/or the lower eyelid medial, central or lateral fat pad), and one or more of the following: presence of edema of one or more of the fat pads, presence of edema along the soft tissue of the upper and/or lower eyelids, presence of malar mounds due to edema, presence of malar edema, and presence of mild festoons aggravated by edema.

In yet another embodiment, a subject is scored as Grade 3 where the subject exhibits pseudoherniation of the three lower eyelid fat pads (e.g., lower eyelid medial, central or lateral fat pads) without any associated periorbital, malar and/or eyelid edema.

In another embodiment, a subject is scored as Grade 3E where the subject exhibits pseudoherniation of the three lower eyelid fat pads (e.g., lower eyelid medial, central or lateral fat pads), and one or more of the following: presence of edema of one or more of the fat pads, presence of edema along the soft tissue of the upper and/or lower eyelids, presence of malar mounds due to edema, presence of malar edema, and presence of mild festoons aggravated by edema.

In another embodiment, a subject is scored as Grade 3+ where the subject exhibits pseudoherniation of the three lower eyelid fat pads with moderate to severe festoons and/or malar mounds secondary to fat deposition or descent/hypertrophy of the orbicularis oculi muscle, and without any associated periorbital, malar or eyelid edema.

In another embodiment, a subject is scored as Grade 3+E where the subject exhibits pseudoherniation of the three lower eyelid fat pads with moderate to severe festoons and/or malar mounds secondary to fat deposition or descent/hypertrophy of the orbicularis oculi muscle with one or more of the following: presence of edema of one or more of the fat pads, presence of edema along the soft tissue of the upper and/or lower eyelids, presence of malar mounds aggravated by edema, presence of localized malar edema, and presence of festoons aggravated by edema.

Malar mounds or festoons are aggravated by edema in a subject where they are more pronounced (larger in surface area and/or volume) due to thyroid disease, allergies, medications, nephrotic syndrome, inflammatory disorders, dietary sensitives (e.g., alcohol, salt, gluten, dairy, or processed foods). Additionally or alternatively, malar mounds or festoons may be aggravated by edema depending on the time of day such as morning versus evening. In some embodiments, the festoons are mild festoons.

A subject scored as Grade 0 may be administered a composition that comprises a protein having hyaluronidase activity to the periorbital region of the subject. A subject scored as Grade 1, Grade 2 or Grade 3 may be treated by surgical removal of a portion of one or more of the fat pads. The subject scored as Grade 0E, 1E, 2E, 3E, or 3+E may be administered a composition that comprises a protein having hyaluronidase activity to the periorbital region of the subject, and optionally treated by surgical removal of a portion of one or more of the fat pads.

In some embodiments, a subject's left eye is given a PEFAS score and the subject's right eye is given a PEFAS score. In other embodiments, only a subject's left or right eye is given a PEFAS score.

As used herein the terms mild, moderate, and severe refer to the degree of severity of a condition exhibited by the bottom, middle, and top third of patients, respectively, that have the condition. The lower third of patients have the least severe degree of the condition and the top third of patients have the highest degree of severity of the condition. For example, a patient with a mild festoons has a severity of festoons that falls within the bottom third of patients examined by a medical practitioner. Additionally, for example, a patient with moderate festoons has a severity of festoons that falls within the middle third of patients examined by a medical practitioner. Further, for example, a patient with severe festoons has a severity of festoons that falls within the top third of patients examined by a medical practitioner.

Alternatively, the present disclosure provides methods for diagnosing an etiology of upper and/or lower eyelid puffiness (e.g., whether the periorbital puffiness is due to edema or a structural change) based on an eyelid squint test. Such methods comprise examining a subject with squinted eye; and determining if upper and/or lower eyelid puffiness does not improve, improves, partially improves, or worsens. The etiology of the upper and/or lower eyelid puffiness is diagnosed to be anterior to the orbicularis oculi muscle if the puffiness does not improve, the etiology of the upper and/or lower eyelid puffiness is diagnosed to be posterior to the orbicularis oculi muscle if the puffiness improves, the etiology of the upper and/or lower eyelid puffiness is diagnosed to be anterior and posterior to the orbicularis oculi muscle if the puffiness partially improves, or the puffiness is diagnosed to be secondary to hypertrophy of the orbicularis muscle or if the puffiness worsens.

In an embodiment, the subject is in an upright position with head in a Frankfort horizontal plane. In a further embodiment, the methods further comprise the step of instructing the subject to squint or tighten the orbicularis oculi muscle.

In an embodiment where the etiology of the upper and/or lower eyelid puffiness is determined to be anterior to the orbicularis oculi muscle the method further comprises administering a protein having hyaluronidase activity (e.g., as described herein) into the soft tissue anterior to the orbicularis oculi muscle.

In an embodiment where the etiology of the upper and/or lower eyelid puffiness is determined to be posterior to the orbicularis oculi muscle, the method further comprises the step of determining if the upper and/or lower eyelid puffiness is secondary to pseudoherniation of upper and/or lower eyelid fat pads, edema of upper and/or lower eyelid fat pads, or upper and/or lower eyelid fat pad pseudoherniation and edema. Such method includes the following steps. First, puffiness of the lower eyelid fat pads are assessed by asking the subject to look straight up, look up and to the right, and look up and to the left. The puffiness of the lower eyelid fat pads is due to pseudoherniation of the lower eyelid fat pads and surgery is indicated if the lower eyelid fat pads protrude and are individually isolated. In contrast, the puffiness is due to pseudoherniation and edema of the lower eyelid fat pads if the lower eyelid fat pads protrude and are not individually isolated. Second, a protein having hyaluronidase activity is then injected into the lower eyelid fat pads to determine the extent of edema of the lower eyelid fat pads. Third, the method may further comprise resecting a portion of the lower eyelid fat pads after assessment of the extent of edema to avoid over resection of the fat pad(s). Next, the puffiness of the upper eyelid fat pads are assessed by asking the subject to look straight down, look down and to the right, and look down and to the left. The puffiness of the upper eyelid fat pads is due to pseudoherniation of upper eyelid fat pads and surgery is indicated if the upper eyelid fat pads protrude and are individually isolated. In contrast, the puffiness is due to pseudoherniation and edema of upper eyelid fat pads if the upper eyelid fat pads protrude and are not individually isolated. Second, a protein having hyaluronidase activity is then injected into the upper eyelid fat pads to determine the extent of edema of the eyelid fat pads. Third, the method may further comprise resecting a portion of the lower eyelid fat pads after assessment of the extent of edema to avoid over resection of the fat pad(s).

In an embodiment where the etiology of the upper and/or lower eyelid puffiness is determined to be anterior and posterior to the orbicularis oculi muscle, the method further comprises injecting a protein having hyaluronidase activity into the upper and/or lower eyelid fat pads.

In an embodiment where the etiology of the upper and/or lower eyelid puffiness is determined to be anterior and posterior to the orbicularis oculi muscle, and wherein the method further comprises assessing whether the puffiness is partially due to pseudoherniation of eyelid fat pads or edema of the fat pads, or eyelid fat pad pseudoherniation and edema. Such method includes the following steps. First, puffiness of the lower eyelid fat pads are assessed by asking the subject to look straight up, look up and to the right, and look up and to the left. The puffiness of the lower eyelid fat pads is due to pseudoherniation of the lower eyelid fat pads and surgery is indicated if the lower eyelid fat pads protrude and are individually isolated. In contrast, the puffiness is due to pseudoherniation and edema of the lower eyelid fat pads if the lower eyelid fat pads protrude and are not individually isolated. Second, a protein having hyaluronidase activity is then injected into the lower eyelid fat pads to determine the extent of edema of the lower eyelid fat pads. Third, the method may further comprise resecting a portion of the lower eyelid fat pads after assessment of the extent of edema to avoid over resection of the fat pad(s). Next, the puffiness of the upper eyelid fat pads are assessed by asking the subject to look straight down, look down and to the right, and look down and to the left. The puffiness of the upper eyelid fat pads is due to pseudoherniation of upper eyelid fat pads and surgery is indicated if the upper eyelid fat pads protrude and are individually isolated. In contrast, the puffiness is due to pseudoherniation and edema of upper eyelid fat pads if the upper eyelid fat pads protrude and are not individually isolated. Second, a protein having hyaluronidase activity is then injected into the upper eyelid fat pads to determine the extent of edema of the eyelid fat pads. Third, the method may further comprise resecting a portion of the lower eyelid fat pads after assessment of the extent of edema to avoid over resection of the fat pad(s).

The present disclosure also provides methods for determining an etiology of periorbital puffiness by performing an eyelid squint test (e.g., asking or having a patient squint their eyes); and observing an impact of a movement of an orbicularis oculi muscle on protrusion of eyelid fat pads, wherein the etiology of the upper and/or lower eyelid puffiness is diagnosed to be anterior to the orbicularis oculi muscle if the puffiness does not improve, wherein the etiology of the upper and/or lower eyelid puffiness is diagnosed to be posterior to the orbicularis oculi muscle if the puffiness improves, wherein the etiology of the upper and/or lower eyelid puffiness is diagnosed to be anterior and posterior to the orbicularis oculi muscle if the puffiness partially improves, or wherein the puffiness is diagnosed to be secondary to hypertrophy of the orbicularis muscle or if the puffiness worsens.

Methods for Treating a Subject Exhibiting Periorbital Puffiness

The present disclosure provides methods for treating a subject exhibiting periorbital puffiness (fullness). Such methods may comprise determining if periorbital fullness exhibited by a patient is due to edema or a structural change (e.g., herniation of one or more of the eyelid fat pads) in their periorbital region.

In an embodiment, the methods comprise administering an initial dose of a composition that comprises a protein having hyaluronidase activity to one or more sites in the periorbital region of the subject, assessing the periorbital region at a predetermined amount of time (e.g., is 5 minutes, 15 minutes, 30 minutes, 1 hour, 24 hours, or 1 week) after the administration of the composition, and determining whether there is an improvement in the periorbital fullness (i.e., whether the puffiness has decreased).

In an embodiment, no improvement in the periorbital puffiness indicates that the periorbital puffiness is due to a structural change and that the protein having hyaluronidase activity is contraindicated for treatment of periorbital puffiness in the subject. In other embodiments, a partial improvement in the periorbital puffiness indicates that the periorbital puffiness is secondary to both edema and a structural change and that the protein having hyaluronidase activity is indicated for treatment of periorbital puffiness in the subject. In another embodiment, an improvement in the periorbital puffiness indicates that the periorbital puffiness is secondary to edema and that the protein having hyaluronidase activity is indicated for treatment of periorbital puffiness in the subject.

The compositions can be formulated in lyophilized or liquid form. Where the compositions are provided in lyophilized form they can be reconstituted just prior to use by an appropriate buffer, for example, a sterile saline solution. The compositions can be provided together or separately. The compositions can be packaged as a kit.

The compositions can be formulated into any suitable pharmaceutical preparations for subcutaneous administration such as solutions, suspensions, powders, or sustained release formulations. Typically, the compositions are formulated into pharmaceutical compositions using techniques and procedures well known in the art (see e.g., Ansel Introduction to Pharmaceutical Dosage Forms, Fourth Edition, 1985, 126). Pharmaceutically acceptable compositions are prepared in view of approvals for a regulatory agency or other agency prepared in accordance with generally recognized pharmacopeia for use in animals and in humans. The formulation should suit the mode of administration.

Pharmaceutical compositions can include carriers such as a diluent, adjuvant, excipient, or vehicle with which a hyaluronidase or IG is administered. Examples of suitable pharmaceutical carriers are described in "Remington's Pharmaceutical Sciences" by E. W. Martin. Such compositions will contain a therapeutically effective amount of the compound, generally in purified form or partially purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Water is a typical carrier when the pharmaceutical composition is administered intravenously. Saline solutions and aqueous dextrose and glycerol solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. A composition, if desired, also can contain minor amounts of wetting or emulsifying agents, or pH buffering agents, for example, acetate, sodium citrate, cyclodextrine derivatives, sorbitan monolaurate, triethanolamine sodium acetate, triethanolamine oleate, and other such agents.

Pharmaceutically therapeutically active compounds and derivatives thereof are typically formulated and administered in unit dosage forms or multiple dosage forms. Each unit dose contains a predetermined quantity of therapeutically active compound sufficient to produce the desired therapeutic effect, in association with the required pharmaceutical carrier, vehicle or diluent. Examples of unit dose forms include ampoules and syringes and individually packaged tablets or capsules. Unit dose forms can be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses that are not segregated in packaging. Generally, dosage forms or compositions containing active ingredient in the range of 0.005% to 100% with the balance made up from non-toxic carrier can be prepared.

Compositions provided herein typically are formulated for administration by subcutaneous route, although other routes of administration are contemplated, such as any route known to those of skill in the art. Formulations suited for such routes are known to one of skill in the art. Administration can be local, topical or systemic depending upon the locus of treatment. Local administration to an area in need of treatment can be achieved by, for example, but not limited to, local infusion during surgery, topical application, transdermal patch, or by injection. Compositions also can be administered with other biologically active agents, either sequentially, intermittently or in the same composition. Thus, in one example, local administration can be achieved by injection, such as from a syringe or other article of manufacture containing a injection device such as a needle or an injection device containing multiple needles. In another example, local administration can be achieved by infusion, which can be facilitated by the use of a pump or other similar device, or by a transdermal patch. Pharmaceutical compositions can be formulated in dosage forms appropriate for each route of administration.

Subcutaneous administration, generally characterized by injection or infusion, is contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. The pharmaceutical compositions may contain other minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such compositions is highly dependent on the specific nature thereof, as well as the activity of the compound and the needs of the subject.

Injectables are designed for local and systemic administration. For purposes herein, local administration is desired for direct administration to the affected area. The solutions may be either aqueous or nonaqueous.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers, which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose.

Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEENs 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art. The unit-dose parenteral preparations are packaged in an ampoule, a vial or a syringe with a needle. The volume of liquid solution or reconstituted powder preparation, containing the pharmaceutically active compound, is a function of the disease to be treated and the particular article of manufacture chosen for package.

In one example, a pharmaceutical preparation can be in liquid form, for example, solutions, syrups or suspensions. If provided in liquid form, the pharmaceutical preparations can be provided as a concentrated preparation to be diluted to a therapeutically effective concentration before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). In another example, pharmaceutical preparations can be presented in lyophilized form for reconstitution with water or other suitable vehicle before use.

Administration methods can be employed to decrease the exposure of the hyaluronidase to degradative processes, such as proteolytic degradation and immunological intervention via antigenic and immunogenic responses. Examples of such methods include local administration at the site of treatment. Pegylation of therapeutics has been reported to increase resistance to proteolysis, increase plasma half-life, and decrease antigenicity and immunogenicity. Examples of pegylation methodologies are known in the art (see for example, Lu and Felix, Int. J. Peptide Protein Res., 43: 127-138, 1994; Lu and Felix, Peptide Res., 6: 142-6, 1993; Felix et al., Int. J. Peptide Res., 46: 253-64, 1995; Benhar et al., J. Biol. Chem., 269: 13398-404, 1994; Brumeanu et al., J Immunol., 154: 3088-95, 1995; see also, Caliceti et al. (2003) Adv. Drug Deliv. Rev. 55(10):1261-77 and Molineux (2003) Pharmacotherapy 23 (8 Pt 2):3S-8S). Pegylation also can be used in the delivery of nucleic acid molecules in vivo. For example, pegylation of adenovirus can increase stability and gene transfer (see, e.g., Cheng et al. (2003) Pharm. Res. 20(9): 1444-2. Dosage and Administration.

Typically, a therapeutically effective dose is at or about 1 Unit to 100,000 Units of a soluble hyaluronidase. For example, soluble hyaluronidase can be administered subcutaneously at or about 10 units, 20 Units, 50 Units, 100 Units, 200 Units, 500 Units, 1000 Units, 2000 Units, 5000 Units, 10,000 Units, 30,000 Units, 40,000 Units, 50,000 Units, 60,000 Units, 70,000 Units, 80,000 Units, 90,000 Units, 100,000 Units or more. Typically, volumes of injections or infusions of hyaluronidase contemplated herein are from at or about 0.1 ml, 0.2 ml, 0.3 ml, 0.5 ml, 1 ml, 2 ml, 3 ml, 4 ml, 5 ml, 6 ml, 7 ml, 8 ml, 9 ml, 10 ml, 15 ml, 20 ml, 30 ml, 40 ml, 50 ml or more. The hyaluronidase can be provided as a stock solution at or about 50 U/ml, 100 U/ml, 150 U/ml, 200 U/ml, 400 U/ml or 500 U/ml or can be provided in a more concentrated form, for example at or about 1000 U/ml, 1500 Units/ml, 2000 U/ml, 4000 U/ml or 5000 U/ml for use directly or for dilution to the effective concentration prior to use.

The actual amount of the hyaluronidase to be administered in any given case will be determined by a physician or other skilled person taking into account the relevant circumstances, such as the amount of edema in the tissues, the desired reduction in the puffiness, the potential fat reduction, the age and weight of the patient, the patient's general physical condition, the cause of the condition, and the route of administration.

Other therapeutically efficient amounts of a hyaluronidase will be apparent to a skilled person upon a reading of the present disclosure. For example, a skilled person can determine the maximum safe dosage for healthy subjects based on the dosages used in animal studies by routine methods (see, e.g. Dept. of Health and Human Services "Guidance For Industry: Estimating the Maximum Safe Starting Dose in Initial Clinical Trials for Therapeutics in Adult Healthy Volunteers"), and then administer to subjects in need thereof various dosages below the maximum safe dosage by routine methods and experimentation until a dosage which results in a desirable effect (e.g. reduction in the extent of periorbital puffiness, festoons, or malar puffiness due to edema) is reached.

The therapeutically efficient amount of a hyaluronidase can be present in a formulation (e.g. for topical administration) at between about 0.01 and about 5% (w/v). In some embodiments, the therapeutically effective amount in the formulation can be from about 0.01 to about 1%, about 0.01 to about 2%, about 0.01 to about 3%, and about 0.01 to about 4%. In other embodiments, the therapeutically effective amount in the formulation can be from about 0.01 to about 1%, about 1 to about 2%, about 2 to about 3%, about 3 to about 4%, about 4 to about 5%.

In other embodiments, the therapeutically effective amount of a hyaluronidase in the formulation can be from about 0.01 to about 0.06%, about 0.06 to about 0.11%, about 0.11 to about 0.16%, about 0.16 to about 0.21%, about 0.21 to about 0.26%, about 0.26 to about 0.31%, about 0.31 to about 0.36%, about 0.36 to about 0.41%, about 0.41 to about 0.46%, about 0.46 to about 0.51%, about 0.51 to about 0.56%, about 0.56 to about 0.61%, about 0.61 to about 0.66%, about 0.66 to about 0.71%, about 0.71 to about 0.76%, about 0.76 to about 0.81%, about 0.81 to about 0.86%, about 0.86 to about 0.91%, about 0.91 to about 0.96%, about 0.96 to about 1.01%, about 1.01 to about 1.06%, about 1.06 to about 1.11%, about 1.11 to about 1.16%, about 1.16 to about 1.21%, about 1.21 to about 1.26%, about 1.26 to about 1.31%, about 1.31 to about 1.36%, about 1.36 to about 1.41%, about 1.41 to about 1.46%, about 1.46 to about 1.51%, about 1.51 to about 1.56%, about 1.56 to about 1.61%, about 1.61 to about 1.66%, about 1.66 to about 1.71%, about 1.71 to about 1.76%, about 1.76 to about 1.81%, about 1.81 to about 1.86%, about 1.86 to about 1.91%, about 1.91 to about 1.96%, about 1.96 to about 2.01%, about 2.01 to about 2.06%, about 2.06 to about 2.11%, about 2.11 to about 2.16%, about 2.16 to about 2.21%, about 2.21 to about 2.26%, about 2.26 to about 2.31%, about 2.31 to about 2.36%, about 2.36 to about 2.41%, about 2.41 to about 2.46%, about 2.46 to about 2.51%, about 2.51 to about 2.56%, about 2.56 to about 2.61%, about 2.61 to about 2.66%, about 2.66 to about 2.71%, about 2.71 to about 2.76%, about 2.76 to about 2.81%, about 2.81 to about 2.86%, about 2.86 to about 2.91%, about 2.91 to about 2.96%, about 2.96 to about 3.01%, about 3.01 to about 3.06%, about 3.06 to about 3.11%, about 3.11 to about 3.16%, about 3.16 to about 3.21%, about 3.21 to about 3.26%, about 3.26 to about 3.31%, about 3.31 to about 3.36%, about 3.36 to about 3.41%, about 3.41 to about 3.46%, about 3.46 to about 3.51%, about 3.51 to about 3.56%, about 3.56 to about 3.61%, about 3.61 to about 3.66%, about 3.66 to about 3.71%, about 3.71 to about 3.76%, about 3.76 to about 3.81%, about 3.81 to about 3.86%, about 3.86 to about 3.91%, about 3.91 to about 3.96%, about 3.96 to about 4.01%, about 4.01 to about 4.06%, about 4.06 to about 4.11%, about 4.11 to about 4.16%, about 4.16 to about 4.21%, about 4.21 to about 4.26%, about 4.26 to about 4.31%, about 4.31 to about 4.36%, about 4.36 to about 4.41%, about 4.41 to about 4.46%, about 4.46 to about 4.51%, about 4.51 to about 4.56%, about 4.56 to about 4.61%, about 4.61 to about 4.66%, about 4.66 to about 4.71%, about 4.71 to about 4.76%, about 4.76 to about 4.81%, about 4.81 to about 4.86%, about 4.86 to about 4.91%, about 4.91 to about 4.96%, and about 4.96 to about 5% (w/v).

The therapeutically effective amount can be administered according to a dosing frequency that is identifiable to a skilled person during a time period that is also identifiable to a skilled person. The term "dosing frequency" as used herein, refers to the number of times the compounds described herein are administered to a subject. Exemplary dosing frequencies include administering the effective amount at discrete times during a day such as, for example, once a day (QD), twice a day (BID), three times a day (TID), four times a day (QID), and others identifiable to a skilled person. Other exemplary dosing frequencies include continuous dosing, for example by intravenous infusion, use of a drug pump, use of a transdermal patch, or other methods of continuous dosing identifiable to a skilled person.

The therapeutically effective amount can be administered at a desired dosing frequency for a time period identifiable to a skilled person. For example, a therapeutically effective can be administered once or twice a day (or at another dosing frequency identifiable to a skilled person) for a set period of time (e.g. seven to fourteen days, two to four weeks, one to six months, or for another time period identifiable to a skilled person). As another example, a therapeutically effective amount can be administered once or twice a day (or at another dosing frequency identifiable to a skilled person) for a non-predetermined period of time. A skilled person can determine at various points during the period of time if the administration of the effective amount is to be continued.

Pharmaceutical compositions of hyaluronidase can be packaged as articles of manufacture containing packaging material, a pharmaceutical composition which is effective for treating puffiness, and a label that indicates that the composition is to be used for treating puffiness. Exemplary of articles of manufacture are containers including single chamber and dual chamber containers. The containers include, but are not limited to, tubes, bottles and syringes. The containers can further include a needle for subcutaneous administration.

The articles of manufacture provided herein contain packaging materials. Packaging materials for use in packaging pharmaceutical products are well known to those of skill in the art. See, for example, U.S. Pat. Nos. 5,323,907, 5,033,252 and 5,052,558, each of which is incorporated herein in its entirety. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

A hyaluronidase composition may optionally comprise an anesthetic agent. An anesthetic agent may be a local anesthetic agent, including an anesthetic agent that causes a reversible local anesthesia or a loss of nociception, such as, e.g., aminoamide local anesthetics and aminoester local anesthetics. Non-limiting examples of anesthetic agents may include lidocaine, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, combinations thereof, and salts thereof. Non-limiting examples of aminoester local anesthetics include procaine, chloroprocaine, cocaine, cyclomethycaine, dimethocaine (larocaine), propoxycaine, procaine (novocaine), proparacaine, tetracaine (amethocaine). Non-limiting examples of aminoamide local anesthetics include articaine, bupivacaine, cinchocaine (dibucaine), etidocaine, levobupivacaine, lidocaine (lignocaine), mepivacaine, piperocaine, prilocaine, ropivacaine, trimecaine, or a combination thereof.

The amount of an anesthetic agent included may be an amount effective to reduce pain experienced by an individual upon administration of the composition, such as about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, about 10%, at least about 0.1%, at least about 0.2%, at least about 0.3%, at least about 0.4%, at least about 0.5%, at least about 0.6%, at least about 0.7%, at least about 0.8% at least about 0.9%, at least about 1.0%, at least about 2.0%, at least about 3.0%, at least about 4.0%, at least about 5.0%, at least about 6.0%, at least about 7.0%, at least about 8.0%, at least about 9.0%, at least about 10%, at most about 0.1%, at most about 0.2%, at most about 0.3%, at most about 0.4%, at most about 0.5%, at most about 0.6%, at most about 0.7%, at most about 0.8% at most about 0.9%, at most about 1.0%, at most about 2.0%, at most about 3.0%, at most about 4.0%, at most about 5.0%, at most about 6.0%, at most about 7.0%, at most about 8.0%, at most about 9.0%, at most about 10%, about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0%.

Some hyaluronidase compositions may comprise lidocaine, in free base or salt form (e.g. lidocaine HCl) in an amount of about 0.05% w/w to about 1% w/w; about 0.1% w/w to about 0.5% w/w, or about 0.3% w/w.

Additionally, compositions of hyaluronidase may have a physiologically-acceptable osmolarity, e.g., about 100 mOsm/L, about 150 mOsm/L, about 200 mOsm/L, about 250 mOsm/L, about 300 mOsm/L, about 350 mOsm/L, about 400 mOsm/L, about 450 mOsm/L, about 500 mOsm/L, at least about 100 mOsm/L, at least about 150 mOsm/L, at least about 200 mOsm/L, at least about 250 mOsm/L, at most about 300 mOsm/L, at most about 350 mOsm/L, at most about 400 mOsm/L, at most about 450 mOsm/L, at most about 500 mOsm/L, about 100 mOsm/L to about 500 mOsm/L, about 200 mOsm/L to about 500 mOsm/L, about 200 mOsm/L to about 400 mOsm/L, about 300 mOsm/L to about 400 mOsm/L, about 270 mOsm/L to about 390 mOsm/L, about 225 mOsm/L to about 350 mOsm/L, about 250 mOsm/L to about 325 mOsm/L, about 275 mOsm/L to about 300 mOsm/L, or about 285 mOsm/L to about 290 mOsm/L. Osmolality agents may be used to adjust osmolality. Examples include, but are not limited to, salts such as, e.g., sodium chloride and potassium chloride; and glycerin.

In some embodiments, a composition comprising hyaluronidase is injectable through a needle of, e.g., about 27 gauge; about 30 gauge; about 32 gauge; about 22 gauge or smaller; about 27 gauge or smaller; about 30 gauge or smaller; about 32 gauge or smaller; about 22 gauge to about 35 gauge; about 22 gauge to about 34 gauge; about 22 gauge to about 33 gauge; about 22 gauge to about 32 gauge; about 22 gauge to about 27 gauge; or about 27 gauge to about 32 gauge.

An hyaluronidase composition may be substantially stable at room temperature, e.g., for about 3 months, about 6 months, about 9 months, about 12 months, about 15 months, about 18 months, about 21 months, about 24 months, about 27 months, about 30 months, about 33 months, about 36 months, at least about 3 months, at least about 6 months, at least about 9 months, at least about 12 months, at least about 15 months, at least about 18 months, at least about 21 months, at least about 24 months, at least about 27 months, at least about 30 months, at least about 33 months, at least about 36 months, about 3 months to about 12 months, about 3 months to about 18 months, about 3 months to about 24 months, about 3 months to about 30 months, about 3 months to about 36 months, about 6 months to about 12 months, about 6 months to about 18 months, about 6 months to about 24 months, about 6 months to about 30 months, about 6 months to about 36 months, about 9 months to about 12 months, about 9 months to about 18 months, about 9 months to about 24 months, about 9 months to about 30 months, about 9 months to about 36 months, about 12 months to about 18 months, about 12 months to about 24 months, about 12 months to about 30 months, about 12 months to about 36 months, about 18 months to about 24 months, about 18 months to about 30 months, or about 18 months to about 36 months.

A hyaluronidase may be injected at between about 2 and about 5 sites. In an embodiment, the hyaluronidase is injected at between about 5 and about 10 sites. In an embodiment, the hyaluronidase is injected at between about 10 to about 30 sites. In an embodiment, the hyaluronidase is injected at between about 10 to about 50 sites. At least two of the sites can be separated by a distance of approximately 100 microns to about 5,000 microns. In an embodiment, the distance between injection sites is about 400 to about 600 microns. In an embodiment, the distance between injections sites is about 100 to about 200 microns, about 200 to about 300 microns, about 300 to about 400 microns, about 400 to about 500 microns, about 500 to about 600 microns, about 600 to about 700 microns, about 700 to about 800 microns, about 800 to about 900 microns, or about 900 to about 1,000 microns. In an embodiment, the distance between injection sites is about 1,000 to about 2,000 microns, about 2,000 to about 3,000 microns, about 3,000 to about 4,000 microns, or about 4,000 to about 5,000 microns.

In an embodiment, the protein having hyaluronidase activity is injected into a lateral eyelid fat pad, a medial eyelid fat pad, and/or a central eyelid fat pad. In a further embodiment, 1 to 15 injections, preferably 1 to 3 injections, are made into each of the lateral eyelid fat pad, medial eyelid fat pad, and/or central eyelid fat pad. Preferably, the injections into the medial eyelid fat pad are made at a depth of between about 3 to about 10 mm, more preferably about 5 to about 8 mm. Additionally, the injections into the central eyelid fat pad are preferably made at a depth of between about 3 to about 12 mm, more preferably about 5 to about 10 mm. Furthermore, the injections into the lateral eyelid fats pad are preferably made at a depth of between about 3 to about 11 mm, more preferably about 5 to about 8 mm.

In an embodiment, the protein having hyaluronidase activity is injected into a malar region. In a further embodiment, 1 to 15 injections, preferably 3 to 7 injections, are made into the malar region. Preferably, the injections into the malar region are made at a depth of between about 2 to about 13 mm, more preferably about 5 to about 10 mm.

In some embodiments of any of the aforementioned methods, the hyaluronidase is administered once. In some embodiments of any of the aforementioned methods, administration of an initial dose the hyaluronidase is followed by the administration of one or more subsequent doses of the hyaluronidase. Examples of dosing regimens (e.g., an interval between the first dose and one or more subsequent doses) that can be used in the methods of the disclosure include an interval of about once every week to about once every 12 months, an interval of about once every two weeks to about once every 6 months, an interval of about once every month to about once every 6 months, an interval of about once every month to about once every 3 months, or an interval of about once every 3 months to about once every 6 months. In some embodiments, administration is monthly, every two months, every three months, every four months, every five months, every six months, or upon disease recurrence.

The present disclosure is further illustrated by the following examples, which should not be construed as limiting in any way. The materials and methods as used in the following experimental examples are described below.

EXAMPLES

Example 1: Determination if Periorbital Puffiness is Due to Edema or a Structural Change A patient presented with periorbital puffiness of the periorbital region in both their right and left eye. To determine the etiology of the puffiness 4 injections of 10 U of HYL-ENEX were made in the periorbital region of both the patient's right and left eye. Specifically, the injections were made in the periorbital soft tissues and edematous orbital fat pads. The injections were performed using a 0.5 ml syringe having a 32-gauge needle inserted parallel to the globe, angling away from the globe, to avoid injury to the globe.

The patient's per-orbital regions in their right eye and left eye were examined 30 minutes after the injections of HYLENEX. Visual examination of the right eye indicated that the puffiness had improved (e.g., a decrease in the volume of puffiness) while examination of the left eye indicated that the puffiness had not improved. The patient's puffiness in their right eye was thus determined to be due to edema while the puffiness in their left eye was determined to be due to a structural change (i.e., herniation of the lower eyelid fat pads). The subject's lower eyelid fat pads in their left eye were then surgically resected.

Example 2: Treatment of Periorbital Puffiness Due to Periorbital Edema Using HYLENEX Four patients (Patients A-D) with periorbital puffiness due to edema (as identified in Example 1) of the eyelid fat pads were scored as a Grade 1E, 2E, 3E, or 3+E on the Periorbital Fullness Assessment Scale. A score was given to the upper and lower eyelids in the patient's left and right eye. Patient A's eyes were scored on the PEFAS scale as a L 0/3E (left eye; upper eyelid over lower eyelid) and a R 0/3E (right eye; upper eyelid over lower eyelid). Patient B was scored as a L 2E/2E and a R 2E/2E. Patient C was scored as a L 1/3E and a R 0/3E and Patient D was scored as a L 2E/3+E and a R 2E/3+E.

The patients were subsequently treated with HYLENEX. Briefly, one injection of 30 U HYLENEX was made per periorbital fat pad exhibiting edema and optionally four injections were administered in the periorbital soft tissues using the same dosage. The injections were performed using a 0.5 ml syringe having a 31-gauge needle inserted parallel to the globe, angling away from the globe, to avoid injury to the globe. Specifically, three injections were made into the medial eyelid fat pad, two into the central eyelid fat pad, and three into the lateral eyelid fat pad at a depth of about 6 mm, 8 mm, and 6 mm, respectively. Additionally Patients B and C received 3 to 5 injections in the periorbital soft tissues (e.g., the malar region) at a depth of between about 5 to about 10 mm.

Figure 1B:
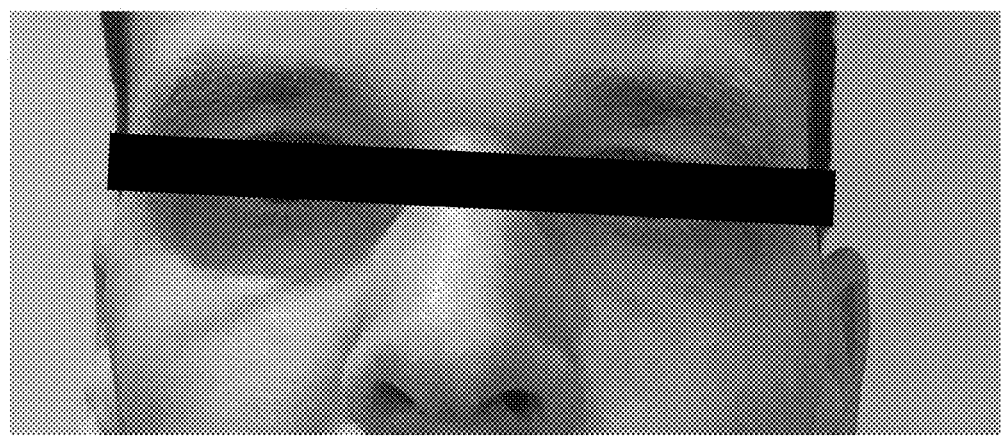
Figure 2A:
FIGS. 2A and 2B show a patient seated in the Frankfort horizontal plane with eye puffiness before (Panel A) and 3 months after (Panel B) subcutaneous injections of a total of 40 U of HYLENEX to four injection sites including: the medial, central and lateral aspects of each of the lower eyelids and the lateral aspect of each of the upper eyelids (10 U per site).
Figure 2B:
Figure 3A:
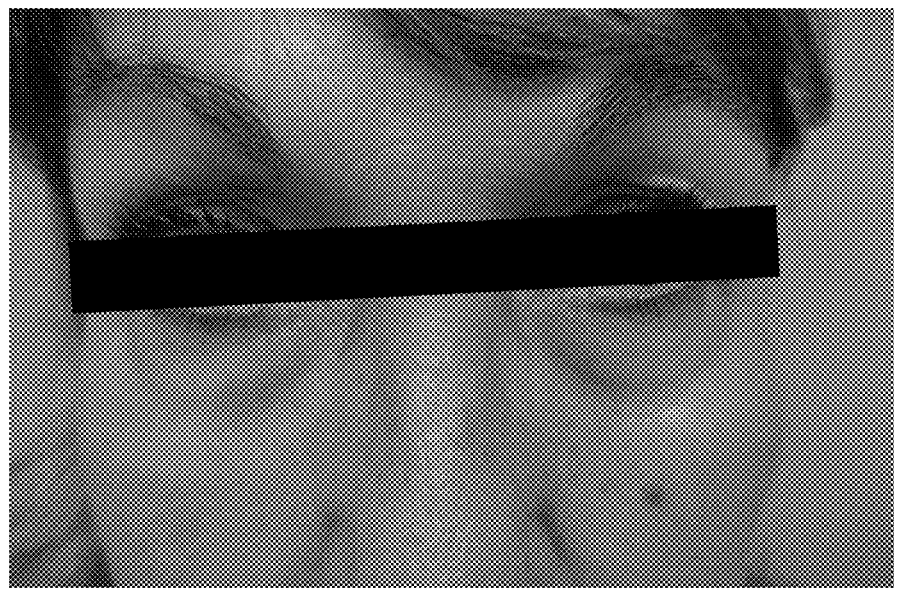
FIGS. 3A and 3B show a patient seated in the Frankfort horizontal plane with eye puffiness before (Panel A) and approximately 1 month after (Panel B) subcutaneous injections of a total of 40 U of HYLENEX to four injection sites including: the medial, central and lateral aspects of each of the lower eyelids and the lateral aspect of each of the upper eyelids (10 U per site).
Figure 3B:
Figure 4A:
FIGS. 4A and 4B show a patient seated in the Frankfort horizontal plane with eye puffiness before (Panel A) and 2 months after (Panel B) subcutaneous injections of a total of 40 U of HYLENEX to four injection sites including: the medial, central and lateral aspects of each of the lower eyelids and the lateral aspect of each of the upper eyelids (10 U per site).
Figure 4B:

Each patient exhibited an improvement in the extent of periorbital puffiness within the first 15-60 minutes after the injections. After treatment, Patient C was followed for 1 month, Patient D was followed for 2 months, and Patients A and B were followed for 3 months. Each patient exhibited a marked reduction in per-orbital (eye) puffiness as compared to the periorbital puffiness that exhibited pre-treatment (see, FIGS. 1-5). The patients were followed for up to 6 months and still exhibit a reduction in periorbital puffiness measured pre-treatment without any adverse effects.

After treatment, the patient's eyes were scored on the PEFAS scale. Patient A's eyes were scored on the PFAS scale as a L 0/0 (left eye; upper eyelid over lower eyelid) and a R 0/0E (right eye; upper eyelid over lower eyelid). Patient B was scored as a L 2E/1E and a R 2E/1. Patient C was scored as a L 1E/1E and a R 0/1 and Patient D was scored as a L 2E/0E and a R 2E/0. Thus, each patient demonstrated an improvement in peri-orbital edema by a decrease in the grade assigned to the periorbital puffiness assigned to both their left and right eyes.

Moreover, an additional 12 patients that exhibit periorbital puffiness were treated according to the regimen described above. Each patient was given an initial Subjective Patient Score of 10. The Subjective Patient Score is based on a scale of 1 to 10 with 10 being the subject's observed starting amount of periorbital puffiness and 0 being no puffiness. Each of the patients scored their puffiness between as a 3 or 4 at 2 weeks, 3 months, and 6 months after their initial treatment.

EMBODIMENTS

Embodiment 1: A method of treating periorbital puffiness in a subject in need thereof, the method comprising:
 a) determining if the periorbital puffiness is due to edema or a structural change; and
 b) administering a protein having hyaluronidase activity to the periorbital region of the subject if the periorbital puffiness is due to edema.

Embodiment 2: The method of embodiment 1, wherein the edema is present in one or more upper and/or lower eyelid fat pads.

Embodiment 3: The method of embodiment 1, wherein the structural change is a herniation of an eyelid fat pad.

Embodiment 4: The method of embodiment 1, the predetermined time is 5 minutes, 15 minutes, 30 minutes, 1 hour, 24 hours, or 1 week after administration of the composition.

Embodiment 5: The method of embodiment 2, wherein no improvement in periorbital puffiness indicates that the periorbital puffiness is due to a structural change.

Embodiment 6: The method of embodiment 2, wherein a partial improvement in periorbital puffiness indicates that the periorbital puffiness is secondary to both edema and a structural change.

Embodiment 7: The method of embodiment 2, wherein an improvement in periorbital puffiness indicates that the periorbital puffiness is secondary to edema.

Embodiment 8: The method of embodiment 2, wherein an improvement includes a reduction in the periorbital puffiness.

Embodiment 9: The method of embodiment 1, wherein the protein having hyaluronidase activity is hyaluronidase.

Embodiment 10: The method of embodiment 1, wherein the hyaluronidase is a recombinant hyaluronidase.

Embodiment 11: The method of embodiment 1, wherein the step of administering is performed by one or more injections into one or more upper and/or lower eyelid fat pads.

Embodiment 12: The method of embodiment 11, wherein each injection includes about 1 to about 1,000 Units of the protein having hyaluronidase activity.

Embodiment 13: A method for treating a subject with periorbital puffiness, the method comprising:
 a.) determining if periorbital puffiness is due to edema or a structural change in the subject;
 b.) administering a protein having hyaluronidase activity to the periorbital region of the subject where the periorbital puffiness is due to edema; and optionally
 c.) surgically resecting a portion of one or more of the upper and/or lower eyelid fat pads.

Embodiment 14: The method of embodiment 13, wherein the protein having hyaluronidase activity is hyaluronidase.

Embodiment 15: The method of embodiment 14, wherein the hyaluronidase is a recombinant hyaluronidase.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary only, with the true scope and spirit of the disclosure being indicated by the following claims. All references, patents, and patent applications referred to in this application are herein incorporated by reference in their entirety.

The invention claimed is:

1. A method for treating periorbital puffiness due to a structural change in a subject in need thereof, the method comprising:
   a. administering an initial dose of a composition comprising a protein having hyaluronidase activity to the periorbital region of the subject;
   b. determining that the periorbital puffiness is due to the structural change;
   c. treating the subject, comprising:
      surgically resecting a portion of one or more upper and/or lower eyelid fat pads, wherein the periorbital puffiness in the subject is unrelated to the use of a hyaluronic acid filler in the periorbital region.

2. The method of claim 1, wherein the structural change is a herniation of the one or more upper and/or lower eyelid fat pads.

3. The method of claim 1, wherein the protein having hyaluronidase activity is hyaluronidase.

4. The method of claim 3, wherein the hyaluronidase is a recombinant hyaluronidase.

5. The method of claim 1, wherein the administering the initial dose of the composition comprises administering one or more injections into one or more upper and/or lower eyelid fat pads.

6. The method of claim 5, wherein each injection comprises about 1 to about 1,000 Units of the protein having hyaluronidase activity.

* * * * *

SEQUENCE LISTING

<160> NUMBER OF SEQ ID NOS: 1

<210> SEQ ID NO 1
<211> LENGTH: 447
<212> TYPE: PRT
<213> ORGANISM: Artificial Sequence
<220> FEATURE:
<223> OTHER INFORMATION: Synthesized

<400> SEQUENCE: 1

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

```
Thr Gly Gln Gly Val Thr Ile Phe Tyr Val Asp Arg Leu Gly Tyr Tyr
    50                  55                  60
Pro Tyr Ile Asp Ser Ile Thr Gly Val Thr Val Asn Gly Gly Ile Pro
65                  70                  75                  80
Gln Lys Ile Ser Leu Gln Asp His Leu Asp Lys Ala Lys Lys Asp Ile
                85                  90                  95
Thr Phe Tyr Met Pro Val Asp Asn Leu Gly Met Ala Val Ile Asp Trp
            100                 105                 110
Glu Glu Trp Arg Pro Thr Trp Ala Arg Asn Trp Lys Pro Lys Asp Val
        115                 120                 125
Tyr Lys Asn Arg Ser Ile Glu Leu Val Gln Gln Asn Val Gln Leu
    130                 135                 140
Ser Leu Thr Glu Ala Thr Glu Lys Ala Lys Gln Glu Phe Glu Lys Ala
145                 150                 155                 160
Gly Lys Asp Phe Leu Val Glu Thr Ile Lys Leu Gly Lys Leu Leu Arg
                165                 170                 175
Pro Asn His Leu Trp Gly Tyr Tyr Leu Phe Pro Asp Cys Tyr Asn His
            180                 185                 190
His Tyr Lys Lys Pro Gly Tyr Asn Gly Ser Cys Phe Asn Val Glu Ile
        195                 200                 205
Lys Arg Asn Asp Asp Leu Ser Trp Leu Trp Asn Glu Ser Thr Ala Leu
    210                 215                 220
Tyr Pro Ser Ile Tyr Leu Asn Thr Gln Gln Ser Pro Val Ala Ala Thr
225                 230                 235                 240
Leu Tyr Val Arg Asn Arg Val Arg Glu Ala Ile Arg Val Ser Lys Ile
                245                 250                 255
Pro Asp Ala Lys Ser Pro Leu Pro Val Phe Ala Tyr Thr Arg Ile Val
            260                 265                 270
Phe Thr Asp Gln Val Leu Lys Phe Leu Ser Gln Asp Glu Leu Val Tyr
        275                 280                 285
Thr Phe Gly Glu Thr Val Ala Leu Gly Ala Ser Gly Ile Val Ile Trp
    290                 295                 300
Gly Thr Leu Ser Ile Met Arg Ser Met Lys Ser Cys Leu Leu Leu Asp
305                 310                 315                 320
Asn Tyr Met Glu Thr Ile Leu Asn Pro Tyr Ile Ile Asn Val Thr Leu
                325                 330                 335
Ala Ala Lys Met Cys Ser Gln Val Leu Cys Gln Glu Gln Gly Val Cys
            340                 345                 350
Ile Arg Lys Asn Trp Asn Ser Ser Asp Tyr Leu His Leu Asn Pro Asp
        355                 360                 365
Asn Phe Ala Ile Gln Leu Glu Lys Gly Gly Lys Phe Thr Val Arg Gly
    370                 375                 380
Lys Pro Thr Leu Glu Asp Leu Glu Gln Phe Ser Glu Lys Phe Tyr Cys
385                 390                 395                 400
Ser Cys Tyr Ser Thr Leu Ser Cys Lys Glu Lys Ala Asp Val Lys Asp
                405                 410                 415
Thr Asp Ala Val Asp Val Cys Ile Ala Asp Gly Val Cys Ile Asp Ala
            420                 425                 430
Phe Leu Lys Pro Pro Met Glu Thr Glu Glu Pro Gln Ile Phe Tyr
        435                 440                 445
```